(12) United States Patent
Tanaka et al.

(10) Patent No.: US 8,158,351 B2
(45) Date of Patent: Apr. 17, 2012

(54) METHOD FOR DETERMINING INFLAMMATORY DISEASE

(75) Inventors: Toshihiro Tanaka, Tokyo (JP); Yusuke Nakamura, Tokyo (JP); Aritoshi Iida, Kanagawa (JP); Kouichi Ozaki, Tokyo (JP); Masatsugu Hori, Hyogo (JP)

(73) Assignee: Riken, Saitama (JP)

( * ) Notice: Subject to any disclaimer, the term of this patent is extended or adjusted under 35 U.S.C. 154(b) by 425 days.

(21) Appl. No.: 12/304,559

(22) PCT Filed: Jun. 15, 2007

(86) PCT No.: PCT/JP2007/062141
§ 371 (c)(1),
(2), (4) Date: Apr. 2, 2009

(87) PCT Pub. No.: WO2007/145326
PCT Pub. Date: Dec. 21, 2007

(65) Prior Publication Data
US 2010/0233684 A1   Sep. 16, 2010

(30) Foreign Application Priority Data

Jun. 15, 2006   (JP) ................................ 2006-165918

(51) Int. Cl.
C12Q 1/68 (2006.01)
C07H 21/02 (2006.01)
C07H 21/04 (2006.01)

(52) U.S. Cl. ...... 435/6.11; 435/6.1; 435/6.18; 536/23.5; 536/24.31

(58) Field of Classification Search .................. None
See application file for complete search history.

(56) References Cited

U.S. PATENT DOCUMENTS

2006/0147920 A1   7/2006   Tanaka et al.
2006/0263774 A1   11/2006  Clark et al.
2007/0190528 A1   8/2007   Tanaka et al.

FOREIGN PATENT DOCUMENTS

JP   2006-515747   6/2006
WO  2004/015100   2/2004
WO  2005/017200   2/2005

OTHER PUBLICATIONS

National Center for Biotechnology Information. National Library of Medicine (Bethesda, MD, USA). SNP Datbase. rs1048990, ss2982370, May 21, 2001.*
Hirschhorn et al. Genetics in Medicine. vol. 4, No. 2, pp. 45-61, Mar. 2002.*
Lucentini et al. The Scientist (2004) vol. 18, p. 20.*
Halushka et al. Nature. Jul. 1999. 22: 239-247.*
Takashima et al. Circ J. 2007. 71: 495-498.*
Liu et al. Atherosclerosis. 2009. 206: 199-203.*
Hinohara et al. J Human Genetics. 2009. 54: 248-251.*
Banerjee et al. Brain Research Bulletin. Sep. 24, 2007. 75: 158-165.*
Sjakste et al. Genetika/Russian J of Genetics. Apr. 2007. 43: 444-450.*
Sjakste et al. Tissue Antigens. Oct. 2004. 64:409, Abstract p. 12-16.*
Marfella, R. et al., J. Am. Coll. Cardiol., vol. 47, pp. 2444-2455 (Epublication May 26, 2006).
Yu, x. et al., Am. J. Physiol. Heart Circ. Physiol., vol. 289, pp. H1960-H1967 (2005).
Edited by Naoyuki Kamatani, "Post Genome Jidai no Iden Tokeigaku 2nd Print" Yodosha Co., Ltd. pp. 58 to 68, and 219 to 230 (2002).
Ozaki K. et al., Nat. Genet., vol. 38, pp. 921-925 (2006).
Takashima, N. et al., Circ. J., vol. 71, pp. 495-498 (2007).
Sjakste, N. et al., Proceeding of the Latvian Academy of Sciences. Section B, vol. 56, pp. 7-16 (2002).
Hermann, J. et al., Cardiovasc. Res. vol. 61, pp. 11-21 (2004).
Pye, J. et al., Am. J. Physiol. Heart Circ. Physiol. vol. 284, pp. H919-H926 (2003).
Hansson G. K., N. Engl. Med. vol. 352, pp. 1685-1695 (2005).
Yamada, Y. et al., N. Engl. J. Med. vol. 347, pp. 1916-1923 (2002).
Ozaki K. et al., Nat. Genet. vol. 32, pp. 650-654 (2002).
Wang L. et al., Science vol. 302, pp. 1578-1581 (2003).
Helgadottir A. et al., Nat. Genet. vol. 36, pp. 233-239 (2004).
Ozaki K. et al., Nature vol. 429, pp. 72-75 (2004).
Cipollonel, F. et al., JAMA vol. 291, pp. 2221-2228 (2004).
Karin, M. et al., Seminars in Immunol. vol. 12, pp. 85-98 (2000).
Maki, C. et al., Cancer Res. vol. 56, pp. 2649-2654 (1996).
Salghetti, S.E. et al., EMBO J. vol. 18, pp. 717-726 (1999).
Dimmeler, S. et al., J. Exp. Med. vol. 189, pp. 1815-1822 (1999).
Beinke, S. et al., Biochem. J. vol. 382, pp. 393-409 (2004).
Coux, O., et al., Annu. Rev. Biochem. vol. 65, pp. 801-847 (1996).
The International HapMap Consortium, Nature vol. 426, pp. 789-796 (2003).
The International HapMap Consortium, Nature Reviews Genetics vol. 5, pp. 467-475 (2004).
Haga, H et al., J. Hum. Genet. vol. 47, pp. 605-610 (2002).
Meiners, S. et al., Circulation vol. 105, pp. 483-489 (2002).
Elliot, P.J., et al., J. Mol. Med. vol. 81, pp. 235-245 (2003).
Dagia, N.M. et al., Am. J. Physiol. Cell Physiol. vol. 285, pp. C813-C822 (2003).
Wojcik C, et al., Stroke vol. 35, pp. 1506-1518 (2004).
Heyninck, K et al. Trends in Biochem. Sci. vol. 30. pp. 1-4 (2005).
U.S. Appl. No. 11/813,450 (Tanaka et al.), which was filed Jul. 6, 2007, "Method of Judging Inflammatory Disease by Using Single Nucleotide Polymorphism.".
Sjakste, T. et al., "Microsatellite genotyping of Chromosome 14q13.2-14q13 in the vicinity of proteasomal gene *PSMA6* and association with Graves' disease in the Latvian population", Immunogenetics 56:238-243, 2004.
Cui, F. et al., "The up-regulation of proteasome subunits and lysosomal proteases in hepatocellular carcinomas of the *HBx* gene knockin transgenic mice", Proteomics 6:498-504, 2006.
Statistical genetics of post-genome age, second impression, 2002, pp. 58-68.
Office Action; patent family member Japanese Patent Application No. 2006-165918; mail date Oct. 18, 2011.

* cited by examiner

*Primary Examiner* — Carla Myers
(74) *Attorney, Agent, or Firm* — Greenblum & Bernstein, PLC

(57) ABSTRACT

It is an object of the present invention to provide a method for determining inflammatory diseases including myocardial infarction as a typical example, which involves identifying polymorphisms associated with myocardial infarction and using the gene polymorphisms, an oligonucleotide that can be used for the method, a kit for diagnosing inflammatory diseases, a therapeutic agent for inflammatory diseases, and the like. The present invention provides a method for determining an inflammatory disease, which comprises detecting at least one type of gene polymorphism existing in a proteasome subunit α type 6 gene.

1 Claim, 3 Drawing Sheets

[Figure 1]
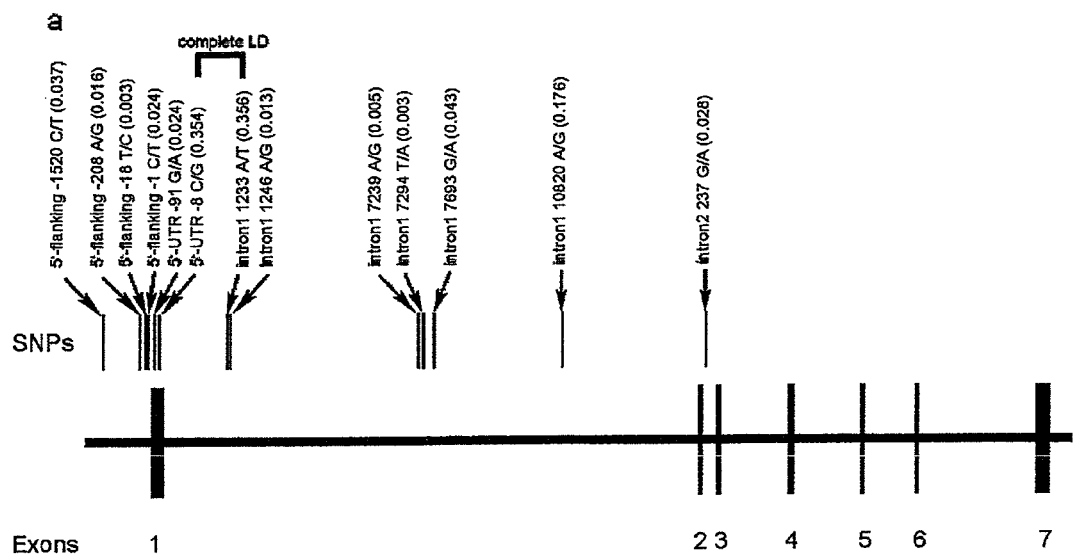

[Figure 2]
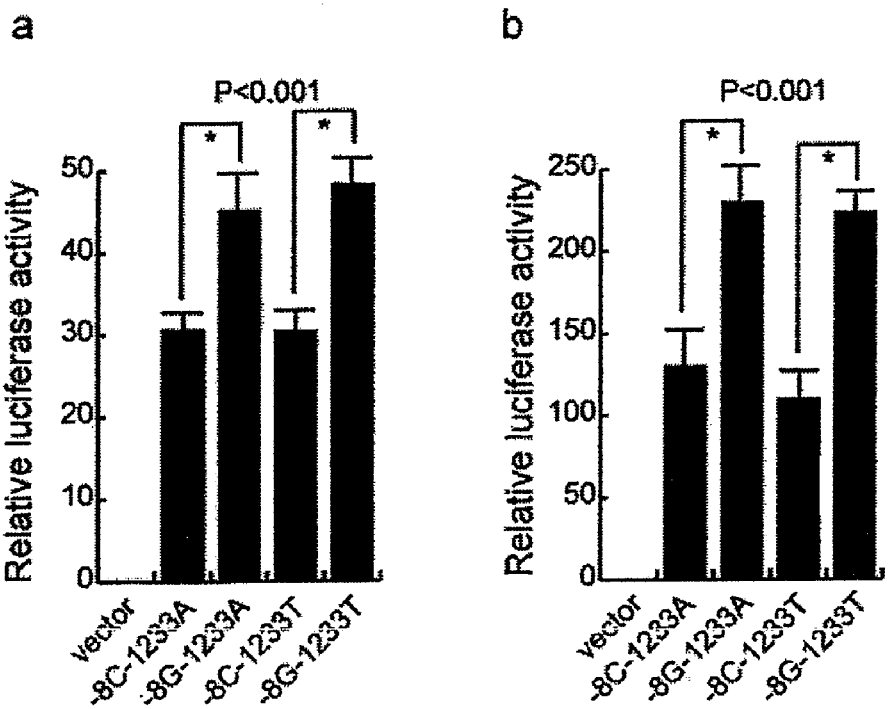
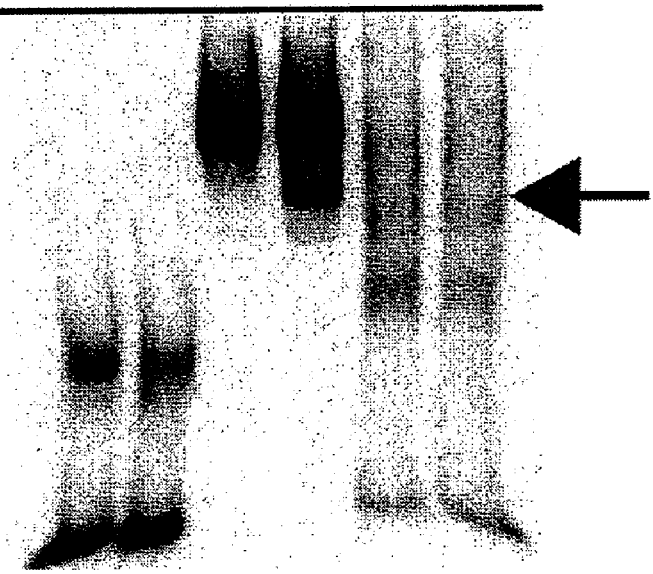

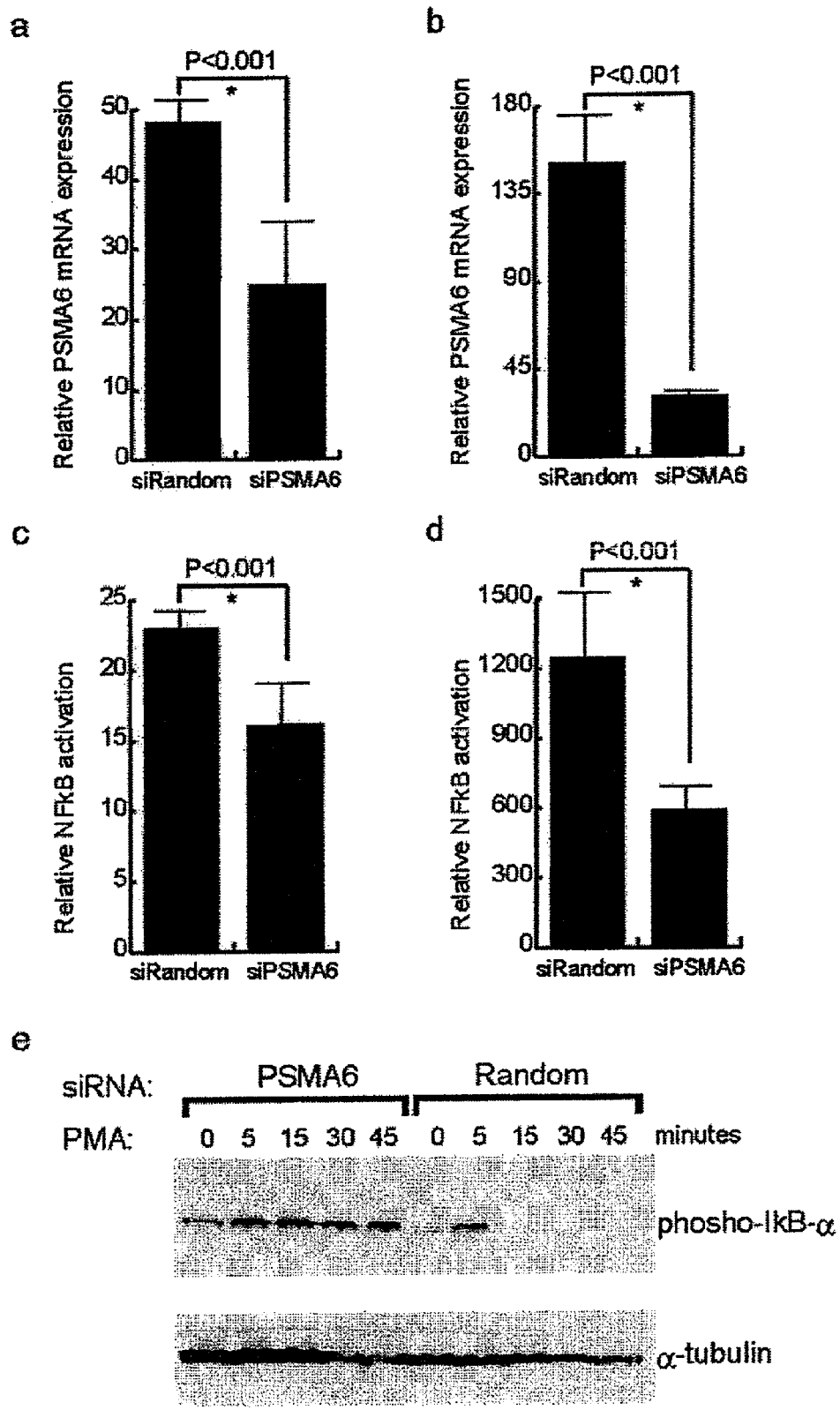
[Figure 3]

SEQUENCE LISTING

```
<160> NUMBER OF SEQ ID NOS: 7

<210> SEQ ID NO 1
<211> LENGTH: 185
<212> TYPE: DNA
<213> ORGANISM: Homo sapiens

<400> SEQUENCE: 1
gcggctggta ccccggaagc agtcgctgca acttccggga ggtgcttgtg tgcctggtgc      60
gggagctacg gggcccaggg attgtgttta aagtagtgct tctaccaaca tgtcccgtgg     120
ttccagcgcc ggttttgacc gccacattac cattttttca cccgagggtc ggctctacca     180
agtag                                                                  185

<210> SEQ ID NO 2
<211> LENGTH: 15441
<212> TYPE: DNA
<213> ORGANISM: Homo sapiens

<400> SEQUENCE: 2
gtgagtgaac caggttcgcc tgtgggccac ctgaattgcc ctgtcatggt acgtgcctgg      60
agcgagcaga cgcggcccgg gtttagtctg gggccgaagc tgggctggag ctgggaaggg     120
agaacggctg aagctggatt gagctctgtg gtgtttgcac ccccgtctgg acgcagggat     180 cggggggcctg aaggcctgtc tctgcagggc gagcggccac actgcgtaga cccaatggag     240
agttaaggaa gatagggctg taatgcctga ctccggcttc gtgaggcccc ttcagttatt     300
gtattctgtc ctggccaggc acaaggtctg tttctaaagg gtaattgatt ccttaacgtc     360
tcaactaaaa tgcctcctct ccgttttcct ttgtttgcag catggacttc tgtggttaat     420
tccacacagg cactcgaagc ctgctatata ccagacactg ctagtcctag gagatacaaa     480
tgtgaatgtt acaccctctt ctatactgaa gctcacagct tagagtgaca gatacgttaa     540
acaaacggat aaaaaaaatt aaaagtgcca atttacaaat atctacagag ttcaagacat     600
ctttgggaat ctgatagaat gagtgactca attctagagc tgctcttgag attggcatcc     660
cctttttacc cacatctgtt tgaatgctcc tgtaatttaa atgccgattc tgagttgtag     720
atgaggtact gtgtactagt ttactgaaga acacctgtag tggaaagaaa ctatcagtta     780
ctcggaatag taatgtattg cgctgaaacg gtgtcaaggt ttaggttatg attataagcc     840
agacccttga tctcttacca tagagaattt agtgtcagga gggcttgatt tacatctggt     900
ccgtgatggt tttattttg aatgagttta gtggctccgt gtcttgcaca gtaatataat     960
```

```
catctgtgct tggaatcata aggagagagt tggtctgtaa atgaggttct cttcacctgt    1020
aaattttaga aatagagtta aagataactt ggaatgaaac tgctcagtgt attactgcat    1080
agtgtatata atgtagcaag aaacatcttg ttggataatt cagtagccct tttaatttat    1140
ccccaattga aaaacatgat taaagataga acaaagagat aactgtmtcc tcaaagaatt    1200
ttcatttatt gtattaaatt cctgagtttt aaataatttt cgtatattag actactgctt    1260
tcagcgttcc attcgtgatt tttaatatgt gaacaggaaa agtcactctg agacctttac    1320
tttgtttcta tatactgtat tgtgaagtcc agccataaag cataatcgtt aatgcttccc    1380
agatttggtg agtggaaagg ctgaacacag tgtcattgtg atggttttaa agatttgga    1440
agagaacatc tatctgaaaa caagttcatt atctagacag aatgattttt tatttatttt    1500
tattttttg agacagagct tcactcttgt tgcctaggct ggagtgcaat ggcgcgatct    1560
cggctccccg caatctccgc ctcccgggtt caagcaattc tgcctcagcc tcccaagtac    1620
tgggattaca ggcatgcgcc accacgcctg gctaattttg tattttagt agagacgagg    1680
tttctccatg ttgatctcga actcccaacc tcaggtgatc cacccacctc ggcctcccaa    1740
agtgctggga ttacaggcgt gagcaccggg cctagcacca gcctgacag aatgatttta    1800
atctctgtga ataacacact ccctctgcta ttcagggcat taattagaca ttgttaggaa    1860
aatgaaagtg aaagagtagt atgagcaagc agtatagtga agagttcagg ccctggagtc    1920
atacatggat tcaaatctct gccctgctcc atactacctg atctgggcac ttgccaggta    1980
tgtaacctta gccttagttt ctcttttccaa agttgggctc ataataattc ttccttaaat    2040
ggtggttttg agaattaaat aaggcaatgt atgtagagtg cttaacgtgt gcctgccaca    2100
tagtaaatgc tcagtgaatg ttattagatg cttgtttgat tctttggccc cccctttttt    2160
ttttggtcta ttagattagt agctctgtat ggaatatttc ccttttatg ggtccttcca    2220
tgcttagttc tccagtaaaa tatatacata atcataatat tctaaatact gtctgtttgt    2280
aaactttaga atcctccaaa gacaaagcat ggaaggatta taggatgcaa gttgttaaca    2340
ttgacagtag gaaaataata ttttaaaaat gggatgatga tgaggggaga ttaatggaag    2400
gtaactatgc tctttatctt ccatacttgg gactcaaaag ataaatgtcg tctaaagttg    2460
atatatcaaa aaatagaggt agacatttaa agttataatg cttggccagg tgcagtgcct    2520
cacacctgta atcccagcac tttgggaggg cgaggtgggc agattacctg aggtcaggag    2580
ttgaagacca gcctgaccaa catggtgaaa ctctgtctct actaaaaata caaaaaacta    2640
gctgcttgtg ctggcgtgcc tgtagtccta cctcctcagg aagctgaggc acaagaatcg    2700
cttgaaccta ggaggcagag gttgcagtga gccaagaccg tgccattgca cctccagact    2760
gggtgacaga gctagactcc atctaaaaaa aaaaaaagt tgtaatgcca atcataatta    2820
taaacatact ttataattat taataacata ttattggcag tgtttgctcc cagggagtgg    2880
agagaaagac ttttttcttt ttttttttt ccctttgaga cagagttgcg ctcttgttgc    2940
ccaggctgga gtgcaatggc cgtgatctca gctcactgaa acctccacct cccaggttca    3000
agcgattctc ctgcctcagc ctcccaagta gctgggatta cagacatgtg ccaccactcc    3060
tggctaattt tgcagtttta atagagatgg ggtttcacca tgttggtctg gctggtcttg    3120
aactcctgac ttcaggtgat ccacccacct cggcctccca aagtgctggg attacaggca    3180
tgagccattg cgctcggcct gaaatatttc tcttaatgta catatgcagg ttgtatgtgt    3240
gtgcatgtat tcatttgtta aaaattgtag aacaccctagc tttgtaatct attttcagga    3300
attgcccaag ttactagagg gaggaggtgc attgtagggg gaatgggact gaggccctag    3360
```

-continued

```
ttggccaaat tcagcctggc tacttgtagg cccttctctt ctgtttgctg atcctttgct    3420
ggataggtct ggcaaggag aagaggagtg gtcatttgga tttgcttgac aggtgtatgt     3480
gagcactgcc tggttgctac aaagaaggga gcgtgctgat agggaactag aaagaaatgg    3540
actggtggag acatactgaa aataaaatgt agaagtgtca ttgtgtattg aagccagaat    3600
tcctgagttc aagtccttac tgcataccaa ctctaagaac ttttatctg taaaataaag     3660 ataataacca cctaccttat agggctttaa ggatttaatt agttaataaa tgtaaagcat    3720
ttaaaacatt gcccggtata tatagtaagc actcaatgtt ttctgggtgt tgtttgttt    3780 gtttgtttgt tgtttttga cagtctca cttggtcgcc caggctagag tgcaatggcg       3840
tgatctcagc tcactgcaac ctctgccttc tgggttcaag tgattctcct gcctcagcct    3900
cccgagtagc tgggattaca ggcgcctgcc accatgcccg gctagttttt gtattttttg    3960
tagaaacagg gtttcactat gttggccagg ttggtcttga actcctgacc tcatgatctg    4020
cccacctcgg cctcccaaag ttctgggatt acaagcgtga gccaccatgc cccgccttca    4080 attagtatt tctgtagggg atactgtcaa gaagaaacaa atggctgatg taaatggagt     4140
cagaaatttc acaaatgact gagaagtact taccatttgc ctcttttgca atttaaaaaa    4200
tattcttatt tcaaagcagt atttctcaac ccaggcttct catgccctct ttgaatctga    4260
tttgaaattc aatgcatgtg tgtgcatgca tacacataca tacatgtgca tatctacata    4320
aatacatata taactacaca gaaaagtga tgggatcaaa tactgctgta ttttcaaacc     4380
tcatattccc cctctctttc cccctccccc agtgccaaga tttctaatga ccccacccc     4440 ttgaggaatc actgttctaa agagtaaaag gttaggaggc actttatagt gaaccacaca    4500
tctcaattat gtagcctaca agtttaggga aaagcaaata agtagcttca aaaaaatctt    4560
aacaaagttt tttttttttt tttttttttt ttttgccaca cagcattgaa attgaatatg    4620
aatatacttt ctttgtccca gtagaacatc ccgttttatt tttatttta ttttttttggg   4680 ggggattgag tctcgctctg tcacccaggc tggagtgcag tgttgcaatc tctgctcact    4740
gcaaactccg cctcctgggt tcacgccgtt ctcctgcctc agcctcctga gtagctggga    4800
ctgtaggcgc ctgcctccga gcccagctaa ttttttatat tttagtaga cgggggttt      4860 caccgtgtta gccaggatgg tctcagtctc ctgacctcgt gatccgcctg cctcggcctc    4920
ccaaagtgct gggattacag gcgtgagcca ccgtgaggcc tgttttttaa taactcatag    4980
aatatgtatc tctcaattca ttttttatttt tcaagcccac gtttatatgg gagaaaatca   5040
tatttacatc ccgaaactct acagcattct aaacaaaatt atgggtggaa aaagtcttga    5100
gttacatttc taataattgg taggacctca gaatcacctg taaatgcttt gcaacacctg    5160
atgagtgaca taaagggaat atatatctct gctgttgttc tcacagcctg agctgtgtac    5220
agtgtgagcc attgtcttgc atcgtgtgcc tgtcctgaac attttgccac cgtgcctttt    5280
atgtttagcc actgtatttt tctagtatac aaatgaatcc cagagaaatt gaggaagtgt    5340
tggggaaaat ggtagggaag gaaacaaagc aaataagata ttactatgga aatgacattt    5400
ctacatacaa ataactgtt gataccattt tgtttgagca aggaagcaat ttacttccta     5460
acctaatggt ttgttgttgg gttcaaccat gaaactgctg gtctttgact aatttttaac    5520
ctgtaaaaat ggcagtttcg tgtggttcaa tctaatactt aggtatttta ctgtgtattt    5580
aagatttaga aaattggggg cttggagtcg agtttaatgc attataattt ttcccattta    5640
aaaactggaa aatggggccg gacacagtgg ctcacacctg taatcccagc actttgggag    5700
gccgaggcag gtggataacc taagtttagg tgttcaagac cagcctggcc cacatggtga    5760
```

```
aaccctatct gtactaaaaa tacaaaaatt agctgggtgt ggtggcgtgc ccctgtagac   5820
ccagctacta gggaggctga gacaggagaa ttgcttgagc ccgggaggtg gaggttgtag   5880
tgagctgaga tcgcactgct gcactctagc ctgggcaaca aagtgagact ccatctcaaa   5940
aaaagaaaaa aaaaggaaa aggaactatg acttattatt ttcttgcata atcttggaca   6000
ttcaagaata gtttactcag ttttagagtt ctgtaagttt ccaaaatttt agcccaaacc   6060
aaagtctttg atcatgtagt gtttaagtac tgttgccaac gtttgaatcc tgactttaaa   6120
aaataaatat cattttaaaa tgctgcccat aaactattat ttttatcttt atttctttat   6180
tattattatt attattttgg agacagagtt tcactcggtt gcccaggctg gagtacagtg   6240
gtgcaatctc agatcactat aacttccgcc tcccaggtta actcaattat cctgcctcag   6300
tctcctgagt agctgggatt acaggcgcgc accaccatac ctggctaatt tttgcatttt   6360
tagtacagac agagtttcac catgttggcc aggctggtct caaactcctg acctcaagtg   6420
atccacctgc ctcggcctcc cgaagtactg gtattatagg cgtgagtcac tgcgtccagc   6480
tatttatttt ttgagacagg gtctcactct gtcgcccagg ctggagtgca gtggtgtaat   6540
catagctcac tgtagcctca aactcttgca ctcaagaaat tctcctgcct cagcttctca   6600
agtagctggg agtacaggta tacaccacca tgctcagata acttttttatt tttagtagag   6660
atgcatcttt ggtgtttccc aggctggtct tgaactcctg gctcaactg atcctcctgc   6720
ctccattccc aaagtgctgg gattataggt gtgagccgcc gcagtgccca gcctcttttt   6780
ttttttttga gatggagtct caccctgtca cccagactgg agtgtagtgg tgcaatctcg   6840
gcttgctgcg acctctgtct cctgggttca agcgattctc ctgcctcagc ccccaatag   6900
ctgggattac aggcgcctgc caccacacct ggctaatttt tgtatttttta atagaggcag   6960
tgtttcacta tgttggttag gctggtcttg aactcctgac ctcaagtgat ccacccgcct   7020
cggcctccca aagtgctggg attacaggcg tgagccacca tgcccagcct cttttttctt   7080
aattggcctt catataccat aggttgtccg tatctgctct aaaccatgat actactgttt   7140
accctgccag tgtttcttta aaagatactc tttaggtgtt gagttgtcta aattctttgc   7200
tctggcagtt tccattttc tggaaattat tataaaacat ttcatggtgg tagtgttaaa   7260
atggggattc atttatacaa gcctttactg aaattacagt gcagcttgat gagtactaaa   7320
tagtataaaa aaggtattac aggaagtgac taactgccta ggagagccgg gaaaggcttc   7380
tcagagatga attggcccag atgaagatta ataaggaaa tttgggggac cagtgcatag   7440
atcagtcagt gtgaatgcag tatagacagt aacaactgaa agagtaaatt atagcaatat   7500
tttgaagggg cttgagtacc atgctagagt ttggactttt ttccatgtgt tttgaacaga   7560
gctagcaggg gtcttaagga atggcgaggt aattaagtaa aataatagga gagttgagtg   7620
tagaaatggg attagaaagg gactgatggt tcacacctgg aattccaaca ctttgggagg   7680
ctaaggcagg aggattgctt gaggccagga gttcgaaact agcctggaca aaataacaag   7740
accttgtctc tgcagaatat ataaaatgaa attagccagg tgtggtagta cacacctgtt   7800
gtcccacata ctctggaggc tgaggtagga ggattgcttg agccgaaagt tcaggttgc   7860
agtgagctac gatcacacca ctgcactcca gcctagacaa cagagtgaga ccttgtctca   7920
gaaaagaaaa taaaaggggg actggtggca ggaagaacaa ttagaagagg tttgctcagt   7980
atcagtaatt catataaacc ctaatgagtg aattaaggta ataagagaga aagggtggag   8040
gggtctcttg agcttatttt tcacattttt attataagaat actttagaca aatgtagata   8100
gactagtaca gtgaccttca tgtacccatc acacagcttc atctgatgtc aatatttttgt   8160
```

```
cagtcttgtt ttctcccttt cccacgcact ttccccgctc ttctagagta cgttaaagca   8220
aatcctaggt ataagaatgg acatttcttg ggaaagggca ggaggttaga gtcaagagtg   8280
ataacccagg tttgtagctt gaaaaattga gtggttagta atacaattat gaaataagga   8340
ctgtaagaaa agcaggttta taagaggaaa gagtttattt ttagacatgt ctgtggctaa   8400
taggcatagg tatttgaaga aatagacatt tgtaattata agtccagagc tagagatgac   8460
agattagtag tgattatcta ggttatagct aaatctctgg tttagggtaa aatcatccag   8520
ggatggagaa ataatagaa ttctgggaaa taccagtatt tcaggagctg gctgaagaga    8580
tgaaagcagt gaagaagatt gagaagggaa gttcagagaa gtaggagagg aagagtagga   8640
atgatattct taacaaagaa ctttaaattt ggctgagcgc agtggttcac acctataatc   8700
ccagcacttt gggaggccga ggcgggtgga tcacttgagg tcaggagttt gagaccagcc   8760
tggccaacat ggtaaaaccc cgtctctact aaaaatacag aaaaactagc tgggtgtggt   8820
ggtgtgtgcc tgtaatccca gctactcagg aagctgaggc aggagaatcg cttgaacctg   8880
ggaggcagag gttgcggcga gccaagattg ctccactgca caccagcctg agtgacagag   8940
tgagactcca tctcaaaaaa aaaaaaactt taaaatccag ttgctcagtt acactagcca   9000
cattttatgt gctcaatagc cacatatgac tagtgactat catattggac attgcaaata   9060
tagaacattg ccagcatcac agaaatttct gttggacagc actggtctat ataaagaacg   9120 agggcccct taatgaatcc tggcaaattc acaggtgcat tctctgttga aagcattttt    9180
ttatatgtaa aatgtttttt attttgtgag acaaagtttt atgtggtagg gaagatactc   9240
ttttgtggct tttaccttttt gcattattta agcaataagc atgtattcat ttattagtt   9300 cagggatgac agacacaaat gcttacacag accagataag taatgccagt gagtaaaaca   9360
ggctgagtga aagataacag gaaatggtgg gacctgtgga aaactgcaaa acacctgctc   9420
agcttaggtg attttttttt tctttgtggc cagttgctat gtgggattga agatcaagtg   9480
ttactagaat tttttttttt ctaggaaaaa atcacatctc taaagaccct ctgcctgctt   9540
ttgccatata aggtaacatt cacaggttcc agggactagg acatagatat attttgggga   9600
tgcatttacc aacctaccag aggggttaatg attttattgg ctcaaagaac cagttttga   9660 cttagctggt ttttctcttg ttgtctgtta ctgtttcttg atttctggcc atgttgtcca   9720
ggctggtctt aaacttctgg gctcaagcga tcctccccat tcagcctccc aaagcagtgg   9780
gattacaagc atgagccatc acacacagcc agaatcacta caaatttagt ggtgtttaaa   9840
caacacacac ttattatgtc atagtttctt tatgttttct atttgttttt ctctgttttc   9900
aaaatttttt ctattttggg ttttcagaca ttggaccata atgaatctat atgtgattt    9960 ctgtttcat tttgcttgga gttttctgag gttctttaat ctgaaatttt tttgtctttt   10020
gccatatttt taacattttt agccattatt tcttcagatt ttgttttccg attctttgct   10080
ctccatatag gactccagtt gtacatatct tacacattt tgatgtagacc cacagattcg   10140 ttgtttttt caactatttt ttctgccttt ttaagattgg atcatttgat acattttcat   10200
attcactcac tctttccttt ctcatctcca ttctacagtt acgtccattt ggtgaatttt   10260 taaatttac gtattatatt tttcagttct acaatttcct tttgcttctt tcatttttc    10320 tttgctgaga tttcctatca ttttcattt tgagaacatt ttccatcatg tcattgagca   10380
tagttataat ggttgttttt aattctttgc taatacagca acatctgggt cgtctcagga   10440 ttgttcttt tgagaattaa acacaatatt cctggttttt gttgtttggt tttggttttg   10500
gttttttagt ttgacttgat ttgttttttg gtatattgag agttccggat tgtatcctgg   10560
```

```
acatttatga atgttatttt atgaagactg tggattctgt tatatttctc caaagagtat    10620
tgacttgttt tgttctaata ggcagttaat ttggttattc tcaagctaca aagtctgtct    10680
cttgggtggc atcttaaatc tcactcggtt tcttttatcc ttaactaggc cgcttggagt    10740
ctgccttgtg tgtgttgtta tggaatctgc tagagatttg ggcagtgttt atatatagaa    10800
gttgggactc tcactctcta gtgctctggt ttctctccct tgttttctgg cagctattgt    10860
taccccaaac tgttctctag ttcttcaggc caaaaagact gagttttctg tgggagttca    10920
gcctttactg ctctcagatt atgagccaca aaaatgggaa actcaactca tgccattcct    10980
ttctcccaac tgttgacttc ccctctagaa tctgactttg tggtgtcttt aggtagtgt    11040
tgttttgttt agagttagta ctttttattt gtggagggct gatctgatag aagctttatt    11100
agccatatca ggatcagaat caagaagcac tttgaaagtt gtacagctag tcctccatat    11160
tcaacccata ttcatgggtt catcatccat ggattcaacc agctgcagat cataaatatt    11220
cagggaaaaa attgctcctg tactgaacat gtacagattt ttttcttgtc attattcgct    11280
aaacaatgta gtataacaac tatttagcat ttacattgta ttagctagtg tagtgtaagc    11340
tagagataat ttcttttcttt tttttttttt aaacggagtc tcactcattg tattagctcg    11400
tgtagtgtaa gctagagata atttctttct tttttttta gacggagtct cgctctgtag    11460
cccaggctgg agtgtagtgg tgcaatctca gctcactgca acctccacct cccaggttcc    11520
agcgattttc ctgcctcagc ctcctgagta gctgggatta caggcacctg ccaccatgtc    11580
tggctaattt ttgtattttt aatagagatg cggtttcacc atgtcggcca ggatggtctt    11640
gaactcctga cttcaggtga tctgcctgtc tctgcctccc aaagtgctgg gattacaggt    11700
gtcagccacc acgcctggcc aagctaggga taatttcaag tatacaggag gatatacata    11760
ggcgatgtgc aaatactgtg ccattttata tcagagactt gagtttctgt ggattttgga    11820
atccatggga ggtcctagaa ccaatcccca caaatagcga ggcaccagct acattttaga    11880
agttatttgt agtgtaggct gagcgcggtc gctcacacct gtaatcccag catctgggag    11940
gccgaggtgg gtgtactacc tgaggtcagg agttcaagac cagcctggcc aacatggcga    12000
aacctcgtct ctactaaaaa tacaaaaatt agctgggcgt ggttgtgcac acctgtaatc    12060
ccagctactc gggaggctca ggcagaattg ctccaaccca ggaggcaggg gttgcagtaa    12120
gccaagattg caccactgca ctccaacctg ggcgacagag tgaaactcca tctcaaaaaa    12180
aaaaaaaaaa gttatttgta gtgtaatggg atggtaaaat tttgctatta taattaacca    12240
attaaattgg gggttatggc tcatacctgc tgtaatccca gctactccag aagccgaggc    12300
aagaggatca tttgaggcca agagtttgag accagcctga gcaatgtagt gagacccat    12360
ctctaaaaaa ttgttttaaa ttaggcatgg tgatacccac ctgtagtctc agctgctcag    12420
gagactgaag tgggagggtc tgaatcagaa gtttgaggct gtggtgagct atgattgtgc    12480
cactgcactc agcctgggtg acagagcaag atgctgtctc ttgctcaata atgataataa    12540
tgataaaacc agttaaatcc aagccatatt tgaagatttc ttttctttg tttctttttt    12600
ttttttttga aatggggtct tgctctgttg cccaggctgg agtacggtgg tgtgagcacg    12660
gctcactgca gcctcgacct cctgggctca agtgatcctc ttgcctcagc ctcccaagga    12720
actgggacca caggtgtacc accatgccta gctaacattt ttttgtagag acagggtctt    12780
gccatgttgc ccaggctggc ctgggactcc ggggctcaag cagtcctccc accttggctt    12840
cccaaattgc taggattaca gatgtgagcc actgcaccca gctgaggatt tcctttaagg    12900
tgatttttct agaatcattt ttgctctgtt cttttgttct ctcttaaata gttagccatt    12960
```

```
tagaaatatt tgatgattta ttacagtttc tattaaaaga gattctttag cctgataggc    13020
agtagctttc ttagctggtc gtcatcacct gtggcttttt gaacagatga ggccttggct    13080
cagactcagt gcccagagtg acactcgaag acagaatttt gaaataatct gttatatgtc    13140
aaaatgtaaa taatgattgg gattatgaat aattatttaa aagttatctt ctgtgttttc    13200
atattttcta ccatgagcat gtattgattt tgttgctttt cccctgatt acaaaatatg     13260 tgcccaggcc aggaacagtg gctcatgcct gtaatcctaa ggtgggagga tcacttgagc    13320
cagagtttga gaccagcctg gcgacatag caagacccca tatctatttt taactaaaaa    13380
taaaataaac aggccaggca tggtggctca tccctgtaat cccatcactt tgggagtctg    13440
aggtgggagg atcgcttgag tccaggagtt tgagaccagc ctgggcaaca tgggaagact    13500
ccatctctac aggaaaaaaa ttgaaaatta gctgggtgtg gtggtataca cctgtggtcc    13560
cagctactca ggaggctgag gctggaagat cacttgggcc cgggaggtcg aggctgcagt    13620
gagctatgat catgccctgg tgctccagcc taggcaacag agcaagaccc tatctcaaaa    13680
cccaccaaaa tatgtgtcta ttattaaatt taaatattgc agaggctgtc ctggtggctc    13740
acgcctgtaa tctcagcact ttggaatgct gatatgggag gatcgcttga gctcagaagt    13800
tcaagaccag cctgggcaag atagtgagac gtcatctcta ctaaaaattt tttaaaaaag    13860
aaaaatttgg gccaggtgca gtggctcatg cctgtaatcc cagcacttca ggaggctgag    13920
gcaggcagat cacctgaggt caggagttca agaccagcct agtcaacatg gtgaaaccct    13980
gtctttactg aaaatacaaa aactagctgg gtgttgtggc gggcagctgt aatcccaact    14040
actcaggacg aggccgaggc aggagaatcg cttgagcccg ggaggcagag gttgtagtga    14100
gccaagatca tgccactgca ctccagcctg ggtgacagag caagatctgt aatcttactg    14160
tcgaaagaca gccattatca attatgctac atggtgccaa agcagttttt ttgtaagcta    14220
ctattttgat cctagtgttt taaccaatag aatggattga cagcagctag aagtgcataa    14280
gctgaggttt gttatagatg gagtcatatg ttggcctggc atggtggctc acgcctgtaa    14340
tcctaacact ttgggaggcc gaggtgggtg gatcacctga ggtcaggagt tcggcaccag    14400
cctggccaac gtggtgaaac cccatcttta ctaaaaatac aaaaacttag ctgggcatgg    14460
tggtgtgcac ctgtaatccc agctactcag gaggctgagg caggagaatc acttgaacct    14520
gggaagcgga ggttgtagta agccaagatc gtgccacctc actccaacct gggcgacaga    14580
gcgagactcc atctcaaaaa agaaaagagt catatgttgt aggtaacata aaaattgcaa    14640
aaagcatgat ccagaaatat tcaacttggt agacaaaaat taatgcaaaa taatcaaaca    14700
gcaattaaaa cttcatgtgg tcaaattagt tactgaccaa agttaacaa agtattaag     14760 tctagaaaaa atttaaagca gctaaatttg acctgggaaa accagactta gaaataatgg    14820
ccacaaaaaa ccttttaaaa tgacaaaaca tcattgataa agatgcagta tgataaaaat    14880
taaattaaac cattattggg gcggggagtg gtggctcaca cctgtaatcc ctgcactttg    14940
ggatgccaag gcaggtggat cacctgaggt caggagttca agactagcct ggccaacaca    15000
gcgaaacccc gtctctagta aaaatacaaa tattagccag atgtggtggc acgcgcctat    15060
aatcccagct acttaggagg ctgaggcagg agactagcgt taacctggca ggcagaggtt    15120
gcagtgagct caggtcgcac cactgcactc cagcctgggt gacagagcga gactctgttt    15180
aaaaaaagaa aaaaactttt ttggaaattg ggtgcatcag cttaatgaaa ataatttcag    15240
taaaatgaaa atggaagaaa tggagttggt ttaactgtga cttgtggtca ttattattat    15300
tttgactttg cacatcctgg aatgctatat gagcattctg tgttcatgta gctctttctc    15360
```

```
attcttttta atgactatta tttcattgca agaatctaca gtaatttatt ccaacttaaa    15420
aaaaactgtt ctgttttcca g                                             15441

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggcccaggg attgtgtt                                                    18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aatggtaatg tggcggtcaa a                                                21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
aagtagtgct tctaccaac                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aagtagtgct tgtaccaac                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtgtgatcct gcaggttac                                                   19
```

METHOD FOR DETERMINING INFLAMMATORY DISEASE

TECHNICAL FIELD

The present invention relates to a method for determining inflammatory diseases, which comprises detecting gene polymorphisms existing in a proteasome subunit α type 6 gene, an oligonucleotide used in the method, a kit for diagnosing inflammatory diseases comprising the oligonucleotide, and a use thereof. Furthermore, the present invention also relates to a method for screening for therapeutic agents for inflammatory diseases using the proteasome subunit α type 6 gene.

BACKGROUND ART

Inflammation is a cause of rapid progression of atheromatous lesion that causes atheroma formation, rupture of a plaque, and intracelial thrombosis. Thus, inflammation plays an important role in the onset of coronary artery disease (Non-Patent Document 1). Recently, several myocardial infarction-sensitive candidate genes have been identified by linkage analysis and/or patient and control correlation analysis using gene polymorphic markers including single nucleotide polymorphisms (SNPs) (Non-Patent Documents 2 to 7 and Patent Documents 1 and 2). Interestingly, it is suggested that a majority of such gene products be associated with inflammation.

A 26S ubiquitin-proteasome system is a principal proteolytic pathway that plays an important role in the regulation of the protein involved in apoptosis, cell cycle, cell growth/differentiation and inflammation (Non-Patent Documents 8 to 11). One of the most important functions of proteasome associated with an inflammatory pathway is decomposition of an I kappa B (IkB) protein that inhibits activation of a nuclear factor kappa B (NFkB). Herein, NFkB is a main transcriptional factor that regulates the expression of genes associated with inflammation such as cytokine or an adhesion molecule involved in generation of atheroma (Non-Patent Document 8).

[Non-Patent Document 1] Hansson G. K., N. Engl. J. Med. 352, 1685-1695 (2005)
[Non-Patent Document 2] Yamada, Y. et al., N. Engl. J. Med. 347, 1916-1923 (2002)
[Non-Patent Document 3] Ozaki K. et al., Nat Genet. 32, 650-654 (2002)
[Non-Patent Document 4] Wang L. et al., Science 302: 1578-81 (2003)
[Non-Patent Document 5] Helgadottir A. et al., Nat. Genet. 36: 233-239 (2004)
[Non-Patent Document 6] Ozaki, K. et al., Nature 429: 72-75 (2004)
[Non-Patent Document 7] Cipollone, F. et al., JAMA 291: 2221-2228 (2004)
[Non-Patent Document 8] Karin, M. et al., Semin. Immunol. 12: 85-98 (2000)
[Non-Patent Document 9] Maid, C. et al., Cancer Res. 56: 2649-2654 (1996)
[Non-Patent Document 10] Salghetti, S. E. et al., EMBO J. 18: 717-726 (1999)
[Non-Patent Document 11] Dimmeler, S. et al., J. Exp. Med. 189: 1815-1822 (1999)
[Patent Document 1] International Publication WO2004/015100
[Patent Document 2] International Publication WO2005/017200

DISCLOSURE OF THE INVENTION

Problems to be Solved by the Invention

It is an object of the present invention to provide a method for determining inflammatory diseases including myocardial infarction as a typical example, which involves identifying polymorphisms associated with myocardial infarction and using the gene polymorphisms, an oligonucleotide that can be used for the method, a kit for diagnosing inflammatory diseases, a therapeutic agent for inflammatory diseases, and the like.

Means for Solving the Problems

The present inventors had conducted genome-wide patient and control correlation analyses using 92,788 SNP markers. As a result, the inventors had previously found that the functional SNP of a lymphotoxin α gene (LTA) encoding one cytokine generated at the initial stage of a vascular inflammation process gives sensitivity to myocardial infarction (Non-Patent Document 3). When LTA stimulates an LTA receptor, an IkB protein that is an inhibitory partner is decomposed by proteasome, so that NFkB becomes activated (Beinke, S., et al., Biochem. J. 382: 393-409 (2004)). Based on this phenomenon, the inventors have hypothesized that a mutation in a gene encoding a proteasome protein would cause a risk of myocardial infarction. A 20S proteasome composed of a 7α-subunit and a 10β-subunit is a central granule of a 26S proteasome system (Coux, O., et al., Annu. Rev. Biochem. 65: 801-847 (1996)). Based on information from international HapMap database (hapmap.org) (The international HapMap consortium. The International HapMap Project. Nature 426: 789-796 (2003); and The international HapMap consortium. INTEGRATING ETHICS AND SCIENCE IN THE INTERNATIONAL HAPMAP PROJECT. Nature Reviews Genetics 5: 467-475 (2004)), and the JSNP database (snp.ims.u-tokyo.ac.jp) (Haga, H et al., J. Hum. Genet. 47: 605-610 (2002)), the present inventors have selected SNPs, which show a minor allele frequency of over 10% and which cover a majority of haplotypes in the genomic regions of genes encoding these subunits. Subsequently, the inventors have made a comparison among 450 patients suffering from myocardial infarction and 450 controls in terms of genotype frequency in such SNP loci (Tables 1 and 2). As a result, it has been revealed that a single SNP (dbSNP ID: rs1048990) (5'UTR −8C>G) of exon 1 of PSMA6 is significantly associated with myocardial infarction (Tables 1 and 2). Moreover, the present inventors have found the possibility that this SNP affects the transcriptional activity of the gene, thus that the amount of a gene product is thereby changed, and that such change then induces diseases such as myocardial infarction. The present invention has been completed based on such findings.

The present invention provides a method for determining an inflammatory disease, which comprises detecting at least one type of gene polymorphism existing in a proteasome subunit α type 6 gene.

The present invention further provides a method for determining an inflammatory disease, which comprises detecting at least one type of single nucleotide polymorphism existing in the proteasome subunit α type 6 gene.

The present invention further provides a method for determining an inflammatory disease, which comprises detecting at least one type of single nucleotide polymorphism selected from the group consisting of the following (1) to (3):
(1) a C/G polymorphism at nucleotide −8 in the nucleotide sequence of exon 1 of the proteasome subunit α type 6 gene;
(2) an A/T polymorphism at nucleotide 1233 in the nucleotide sequence of intron 1 of the proteasome subunit α type 6 gene; and
(3) a polymorphism that is in a linkage disequilibrium state at a linkage disequilibrium coefficient D' of 0.8 or more with the polymorphism described in (1) or (2) above.

The present invention further provides a method for determining an inflammatory disease, wherein determination is carried out using the expression level or activity of proteasome subunit α type 6 as an indicator.

Preferably, the inflammatory disease is myocardial infarction.

The present invention further provides an oligonucleotide that can hybridize to a sequence of at least 10 continuous nucleotides containing at least one site selected from the group consisting of the following (1) to (3) or to a complementary sequence thereof, and that is used as a probe in the method according to any one of the above.
(1) site −8 in the nucleotide sequence of exon 1 of the proteasome subunit α type 6 gene;
(2) site 1233 in the nucleotide sequence of intron 1 of the proteasome subunit α type 6 gene; and
(3) a polymorphic site that is in a linkage disequilibrium state at a linkage disequilibrium coefficient D' of 0.8 or more with the polymorphism described in (1) or (2) above.

The present invention further provides an oligonucleotide that enables amplification of a sequence of at least 10 continuous nucleotides containing at least one site selected from the group consisting of the following (1) to (3) and/or a complementary sequence thereof, and that is used as a primer in the method according to any one of the above.
(1) site −8 in the nucleotide sequence of exon 1 of the proteasome subunit α type 6 gene;
(2) site 1233 in the nucleotide sequence of intron 1 of the proteasome subunit α type 6 gene; and
(3) a polymorphic site that is in a linkage disequilibrium state at a linkage disequilibrium coefficient D' of 0.8 or more with the polymorphism described in (1) or (2) above.

Preferably, the primer is a forward primer and/or a reverse primer.

The present invention further provides a kit for diagnosing an inflammatory disease, which comprises one or more types of the oligonucleotides according to any one of the above.

Preferably, the inflammatory disease is myocardial infarction.

The present invention further provides a method for analyzing the expression state of proteasome subunit α type 6, which comprises detecting a single nucleotide polymorphism of C/G at nucleotide −8 in the nucleotide sequence of exon 1 of the proteasome subunit α type 6 gene.

The present invention further provides a method for measuring the transcriptional activity of proteasome subunit α type 6, which comprises introducing a proteasome subunit α type 6 gene fragment containing a single nucleotide polymorphism of C/G at nucleotide −8 in the nucleotide sequence of exon 1 of the proteasome subunit α type 6 gene into a cell, culturing the cell, and then analyzing the expression of the gene.

The present invention further provides a method for screening for a substance that inhibits the transcriptional activity of proteasome subunit α type 6, which comprises introducing a proteasome subunit α type 6 gene fragment containing a single nucleotide polymorphism of C/G at nucleotide −8 in the nucleotide sequence of exon 1 of the proteasome subunit α type 6 gene into a cell, culturing the cell in the presence of a candidate substance that inhibits the transcriptional activity of proteasome subunit α type 6, and then analyzing the expression of the gene.

The present invention further provides a substance inhibiting the transcriptional activity of proteasome subunit α type 6, which obtained by the screening method according to the present invention.

Preferably, a transcriptional unit formed by inserting a reporter gene to a site downstream of the proteasome subunit α type 6 gene fragment is introduced into a cell, the cell is cultured, and then the reporter activity is measured so as to analyze the expression of the gene.

Preferably, the reporter gene is a luciferase gene.

The present invention further provides a method for screening for a transcriptional regulatory factor of proteasome subunit α type 6, which comprises allowing a gene fragment containing a single nucleotide polymorphism of C/G at nucleotide −8 in the nucleotide sequence of exon 1 of the proteasome subunit α type 6 gene to come into contact with a sample wherein a transcriptional regulatory factor of proteasome subunit α type 6 is presumed to be present, and detecting the binding of the fragment with the transcriptional regulatory factor.

Preferably, the detection is carried out by gel shift assay.

The present invention further provides a therapeutic agent for an inflammatory disease, which comprises, as an active ingredient, a substance that suppresses the expression or activity of proteasome subunit α type 6.

Preferably, the substance that suppresses the expression or activity of proteasome subunit α type 6 is siRNA or an antibody against the proteasome subunit α type 6.

The present invention further provides a method for screening for a therapeutic agent for an inflammatory disease, which comprises a step of allowing a cell to come into contact with a candidate substance, a step of analyzing the expression level of a gene encoding proteasome subunit α type 6 within the cell, and a step of selecting, as a therapeutic agent for an inflammatory disease, a candidate substance that lowers the expression level of the gene by comparison with a condition where the candidate substance is absent.

Effect of the Invention

According to the method of the present invention, the judgment of the presence or absence of the onset of inflammatory diseases including myocardial infarction as a typical example and the judgment of the probability of the onset of such a disease can be performed accurately and rapidly.

Moreover, it has been demonstrated that, in the neointimal region of an atherosclerotic lesion, ubiquitin is co-localized with an α smooth muscle cell actin, and that a ubiquitin-proteasome system is potentially involved in playing an important role at the initial stage, progressive stage and terminal stage of atheroma (Hermann, J, et al., Cardiovasc. Res. 61: 11-21 (2004)). Furthermore, it has been reported that a pharmacological inhibitor of a ubiquitin-proteasome pathway inhibits activation of NFkB, so as to significantly reduce the myocardial reflux disorder, ischemic myocardial infarction, and atherosclerosis of an experimental animal model (Meiners, S. et al., Circulation 105: 483-489 (2002); Pye, J. et al., Am. J. Physiol. Heart Circ. Physiol. 284: H919-H926; Elliott, P. J., et al., J. Mol. Med. 81: 235-245 (2003); Dagia, N. M. et al., Am. J. Physiol. Cell Physiol. 285: C813-C822 (2003); Wojcik C, et al. Stroke 35: 1506-1518 (2004); and Heyninck, K et al. Trends Biochem. Sci. 30: 1-4 (2005)).

Accordingly, taking into consideration the gene correlation of SNPs of PSMA6 of the present invention and the functional role thereof, it is likely that such a ubiquitin-proteasome pathway plays an important functional role in the onset of myocardial infarction.

BEST MODE FOR CARRYING OUT THE INVENTION

[1] Method for Determining Inflammatory Disease

The method of the present invention is a method for determining the presence or absence of the onset of inflammatory diseases or the possibility of the onset of inflammatory diseases by detecting gene polymorphisms, particularly single nucleotide polymorphisms (SNPs) existing in specific gene showing association with inflammatory diseases.

The above specific gene is a proteasome subunit α type 6 gene. The gene polymorphisms exist on the exon or intron portion of genomic DNA containing this gene.

In the present invention, the expression "detecting at least one type of gene polymorphism (e.g., a single nucleotide polymorphism, etc.) existing in the proteasome subunit α type 6 gene" means both (i) a direct detection of the gene polymorphism (referred to as a "gene polymorphism on the gene side"), and (ii) a detection of the gene polymorphism existing on the complementary sequence of the above gene (referred to as polymorphisms on the complementary side) so as to presume the polymorphisms on the gene from the detection results. However, since nucleotides on the gene and nucleotides on the complementary sequence are not always in a completely complementary relationship, it is preferable to directly detect the polymorphism on the gene.

In addition, examples of a single nucleotide polymorphism used as a detection target in the present invention include gene polymorphisms that exist in the proteasome subunit α type 6 gene. A more specific example is at least one type of single nucleotide polymorphism selected from the group consisting of the following (1) to (3):

(1) a C/G polymorphism at nucleotide −8 in the nucleotide sequence of exon 1 of the proteasome subunit α type 6 gene;
(2) an A/T polymorphism at nucleotide 1233 in the nucleotide sequence of intron 1 of the proteasome subunit α type 6 gene; and
(3) a polymorphism that is in a linkage disequilibrium state at a linkage disequilibrium coefficient D' of 0.8 or more with the polymorphism described in (1) or (2) above.

The nucleotide sequence of the proteasome subunit α type 6 gene (PSMA6 gene) is publicly known. This nucleotide sequence has been registered at the National Center for Biotechnology Information (NCBI) under registration No. NC_000014, for example.

In this specification, there are cases where a nucleotide at position X of exon or intron is indicated with a combination of number X representing the position with a symbol representing the nucleotide. For example, "−8C/G" of exon 1 of the proteasome subunit α type 6 gene indicates C or G at position −8 (a position located 8 nucleotides upstream of the start codon). Exon 1 and the nucleotide sequence upstream thereof are shown in SEQ ID NO: 1 of the sequence listing. The position −8 in the nucleotide sequence of exon 1 corresponds to the nucleotide (C) at position 102 in SEQ ID NO: 1.

In addition, "1233A/T" of intron 1 of the proteasome subunit α type 6 gene indicates A or T at position 1233 in the nucleotide sequence of intron 1. The nucleotide sequence of intron 1 is shown in SEQ ID NO: 2 of the sequence listing. The position 1233 shown in the nucleotide sequence of intron 1 corresponds to the nucleotide at position 1233 in SEQ ID NO: 2.

In the present invention, when the nucleotide at position −8 in the nucleotide sequence of exon 1 of the proteasome subunit α type 6 gene is G, or when the nucleotide at position 1233 in the nucleotide sequence of intron 1 of the proteasome subunit α type 6 gene is T, it can be determined that inflammatory disease has been developed or it is highly likely to be developed.

In contrast, when the nucleotide at position −8 in the nucleotide sequence of exon 1 of the proteasome subunit α type 6 gene is C, or when the nucleotide at position 1233 in the nucleotide sequence of intron 1 of the proteasome subunit α type 6 gene is A, it can be determined that inflammatory disease has not been developed or it is unlikely to be developed.

Further, in the present invention, a polymorphism that is in a linkage disequilibrium state at a linkage disequilibrium coefficient D' of 0.8 or more with the polymorphism described in (1) or (2) above can also be used. The "linkage disequilibrium" means that two alleles are linked to each other and are inherited at a frequency greater than in a case where each of the two alleles is independently inherited. With regard to SNPs markers, a linkage disequilibrium of 22 kb or less on average is maintained in the case of Asian people including Japanese people and Western people. According to a report, in the case of African people, a linkage disequilibrium of 11 kb or less on average is maintained. A group of alleles exhibiting such a linkage disequilibrium is referred to as a haplotype. When a plurality of SNPs are present in the proteasome subunit α type 6 gene locus, a combination of polymorphisms is different depending on individuals. This combination is what is called a haplotype marker, and it shows the diversity of individuals. Using such a haplotype marker, the genetic information of a subject can be correlated with the predisposing cause of inflammatory disease. With regard to two SNPs, each allele of a first SNP is defined as (A, a), and each allele of a second SNP is defined as (B, b). Then, each frequency of four haplotypes (AB, Ab, aB, ab) is defined as $P_{AB}$, $P_{Ab}$, $P_{aB}$, and $P_{ab}$, respectively. Under such conditions, the linkage disequilibrium coefficient D' can be obtained by the following formula:

$$D' = (P_{AB}P_{ab} - P_{Ab}P_{aB})/\text{Min}[(P_{AB}+P_{aB})(P_{aB}+P_{ab}), (P_{AB}+P_{Ab})(P_{Ab}+P_{ab})]$$

wherein $\text{Min}[(P_{AB}+P_{aB})(P_{aB}+P_{ab}), (P_{AB}+P_{Ab})(P_{Ab}+P_{ab})]$ indicates either $(P_{AB}+P_{aB})(P_{aB}+P_{ab})$ or $(P_{AB}+P_{Ab})(P_{Ab}+P_{ab})$, which has a smaller value.

In the present invention, a polymorphism having a linkage disequilibrium coefficient D' of preferably 0.8 or more, more preferably 0.95 or more, further preferably 0.99 or more, and most preferably 1, can be used.

In this specification, "determination" of diseases is used to mean the judgment of the presence or absence of the onset of diseases, the judgment of probabilities of the onset of diseases (prediction of the risk of incidence), elucidation of genetic factors of diseases, and the like.

In addition, such "determination" of diseases can be carried out by combining results obtained by the above method for detecting single nucleotide polymorphisms and results obtained by other polymorphism analyses (VNTR and RFLP) and/or other tests, if desired.

Moreover, in this specification, "inflammatory disease" is not specifically limited, as long as it is a disease confirmed to induce cell adhesion factors or cytokines that are known to correlate with pathologic conditions of inflammation.

Examples of such inflammatory disease include chronic articular rheumatism, systemic erythematodes, inflammatory enteritis, various allergic reactions, bacterial shock, and arteriosclerotic diseases such as myocardial infarction and cerebral apoplexy (particularly myocardial infarction).

(Detection Target)

As a target to be detected for gene polymorphisms, genomic DNA is preferable. In some instances (that is, when a polymorphic site and the sequence of a region adjacent thereto are identical to or completely complementary to a genome), cDNA or mRNA can also be used. Moreover, examples of a sample from which the above targets are collected include any biological samples such as: body fluids such as blood, bone marrow fluids, sperm, peritoneal fluids, and urine; cells of tissues such as liver; and body hair such as hair. Genomic DNA and the like can be extracted, purified, and then prepared from such samples according to standard methods.

(Amplification)

Upon detection of gene polymorphisms, a region containing polymorphisms is first amplified. Amplification is carried out by, for example, the PCR method, or can also be carried out by other known amplification methods such as an NASBA method, an LCR method, an SDA method, and a LAMP method.

Primers are selected so that, for example, in the sequence shown in SEQ ID NO: 1 or 2, a sequence of at least 10 or more, preferably 10 to 100, and more preferably 10 to 50 continuous nucleotides containing the above single nucleotide polymorphism site(s), and/or complementary sequence thereof, is amplified.

The primer may also contain in its sequences one or more substitutions, deletions, or additions, as long as it can function as a primer for amplifying a sequence of a predetermined number of nucleotides containing the above single nucleotide polymorphism site(s).

Primers to be used for amplification may also be selected so that either a forward primer or a reverse primer hybridizes to a single nucleotide polymorphism site and amplification is conducted only when a sample is of a single allele type. Primers can be labeled with fluorescent substances, radioactive substances, or the like, if necessary.

(Detection of Polymorphisms)

Gene polymorphisms can be detected by hybridization with a probe that is specific to a single allele type. Probes may be labeled by appropriate means such as fluorescent substances or radioactive substances, if necessary. Probes are not specifically limited, as long as they contain the above single nucleotide polymorphism site(s), hybridize to a test sample, and confer specificity detectable under detection conditions employed. As a probe, for example, a sequence of at least 10 or more, preferably 10 to 100, and more preferably 10 to 50 continuous nucleotides containing the above single nucleotide polymorphism site(s) contained in the sequences shown in SEQ ID NO: 1 or 2, or oligonucleotides capable of hybridizing to the complementary sequences thereof, can be used. Moreover, an oligonucleotide is preferably selected so that a single nucleotide polymorphism site exists at almost the central portion of the probe. The oligonucleotide may contain in its sequence one or more substitutions, deletions, or additions, as long as it can function as a probe; that is, as long as it can hybridize under conditions where it hybridizes to a sequence of a target allele type, but does not hybridize to sequences of other allele types. Examples of the probe include probes that satisfy the above probe conditions by annealing with genomic DNA to form a circle, such as a single-stranded probe (padlock probe) that is used for amplification by an RCA (rolling circle amplification) method.

Hybridization conditions employed in the present invention are conditions sufficient for distinguishing allele types. Examples of such conditions are stringent conditions wherein hybridization takes place when a sample is of a single allele type, but does not take place when a sample is of another allele type. Here, examples of "stringent conditions" include conditions described in Molecular Cloning: A Laboratory Manual ($2^{nd}$ edition, Sambrook et al., 1989). Specific examples of such conditions include conditions wherein a solution containing 6×SSC (1×SSC composition: 0.15 M NaCl, 0.015 M sodium citrate, pH 7.0), 0.5% SDS, 5×Denhardt, and 100 mg/ml Pacific herring sperm DNA and a probe are together incubated at 65° C. overnight.

A probe with its end fixed on a plate can also be used as a DNA chip. In this case, onto the DNA chip, only a probe corresponding to a single allele type may be fixed, or a probe corresponding to both allele types may be fixed.

Gene polymorphisms can also be detected by a restriction enzyme fragment length polymorphism analytical method (RFLP: Restriction fragment length polymorphism). In this method, sample nucleic acids are digested with restriction enzymes (whether or not nucleic acids are cleaved by restriction enzymes depends on the genotype of a single nucleotide polymorphism site), and then the thus digested fragment sizes are examined to know whether or not the sample nucleic acids are cleaved with the restriction enzymes, whereby the polymorphisms of the sample are analyzed.

Gene polymorphisms may also be detected by directly sequencing the amplified products (direct sequencing method). Sequencing can be carried out by a known method such as a dideoxy method or a Maxam-Gilbert method.

Gene polymorphisms may also be detected by an invader assay. In this method, an invader oligo that has a sequence complementary to a DNA target fragment to be tested to determine the presence or absence of SNP and a complementary oligo (signal probe) that contains a 5'-flap structure and is used for detecting SNP are used. First an invader oligo and a signal probe are caused to hybridize to a target DNA. At this time, the invader oligo and the probe form an invasive structure wherein they overlap at a single nucleotide. Cleavase (flap endonuclease separated from *Archaeoglobus fulgidus*) acts on this portion. When nucleotides of a signal probe at an SNP site and target nucleotides are complementary (no SNPs) to each other, the 5' flip of the signal probe is cleaved. The cleaved 5' flip hybridizes to a FRET (fluorescence resonance energy transfer) probe. On the FRET probe, a fluorescent dye and a quencher (Quencher) are closely adjacent to each other so as to suppress fluorescence. Binding of the 5' flip results in cleavage of a portion of the fluorescent dye by cleavase, so that fluorescence signals can be detected.

Furthermore, to detect gene polymorphisms, a denaturing gradient gel electrophoresis (DGGE) method, single strand conformation polymorphism analysis (SSCP), allele-specific PCR, a hybridization method using ASO (allele-specific oligonucleotide), chemical cleavage of mismatches (CCM), an HET (heteroduplex method) method, a PEX (primer extension) method, an RCA (rolling circle amplification) method, or the like can be used.

[2] Kit for Diagnosing Inflammatory Diseases

A kit for diagnosing inflammatory diseases containing the oligonucleotides as the above primers or probes can be provided. The kit may also contain restriction enzymes, polymerase, nucleoside triphosphate, labeling substances, buffers, and the like to be used for methods for analyzing the above polymorphisms.

[3] Method for Analyzing Expression State of Proteasome Subunit α Type 6

According to the present invention, the expression state of proteasome subunit α type 6 can be analyzed by detecting a single nucleotide polymorphism of C/G at nucleotide −8 in the nucleotide sequence of exon 1 of the proteasome subunit α type 6 gene. Specifically, when the nucleotide at position −8 in the nucleotide sequence of exon 1 of the proteasome subunit α type 6 gene is G, it can be determined that the expression level of proteasome subunit α type 6 is high. When the nucleotide at position −8 in the nucleotide sequence of exon 1 of the proteasome subunit α type 6 gene is C, it can be determined that the expression level of proteasome subunit α type 6 is low.

[4] Method for Measuring Transcriptional Activity of Proteasome Subunit α type 6

According to the present invention, the transcriptional activity of proteasome subunit α type 6 can be measured by introducing a proteasome subunit α type 6 gene fragment containing a single nucleotide polymorphism of C/G at nucleotide −8 in the nucleotide sequence of exon 1 of the proteasome subunit α type 6 gene into a cell, culturing the cell, and then analyzing the expression of the gene.

According to a preferred embodiment of the present invention, the expression of the gene is analyzed by introducing a transcriptional unit formed by inserting a reporter gene to a site downstream of the proteasome subunit α type 6 gene fragment into a cell, culturing the cell, and then measuring the reporter activity.

When a single nucleotide polymorphism exists at a promoter site, a cell into which a system formed by inserting a reporter gene into a site downstream of a gene containing the single nucleotide polymorphism is cultured, and then the reporter activity is measured, so that differences in transcriptional efficiency due to the single nucleotide polymorphism can be measured.

As a reporter gene, a luciferase gene, a chloramphenicol gene, an acetyltransferase gene, a galactosidase gene, or the like may be used herein.

[5] Method for Screening for Substance that Inhibits Transcriptional Activity of Proteasome Subunit α Type 6 Gene In the present invention, a substance that inhibits the transcriptional activity of a proteasome subunit α type 6 gene can be screened for by introducing a proteasome subunit α type 6 gene fragment containing a single nucleotide polymorphism of C/G at nucleotide −8 in the nucleotide sequence of exon 1 of the proteasome subunit α type 6 gene into a cell, culturing the cell in the presence of a candidate substance that inhibits the transcriptional activity of proteasome subunit α type 6, and then analyzing the expression of the gene.

According to a preferred embodiment of the present invention, the expression of the gene is analyzed by introducing a transcriptional unit formed by inserting a reporter gene to a site downstream of the aforementioned proteasome subunit α type 6 gene fragment into a cell, culturing the cell, and then measuring the reporter activity.

For example, a cell, into which a system formed by inserting a reporter gene into a site downstream of a gene having a single nucleotide polymorphism confirmed to result in a significantly high expression level of a proteasome subunit α type 6 gene (e.g., a case where the nucleotide at position −8 in the nucleotide sequence of exon 1 of the proteasome subunit α type 6 gene is G) has been introduced, is cultured in cases of both the presence and the absence of a candidate substance. If the resulting reporter activity decreases when the cell is cultured in the presence of the candidate substance, the candidate substance can be selected as a substance that inhibits the transcriptional activity of proteasome subunit α type 6.

As reporter genes, the aforementioned genes are used.

As candidate substances, any substances can be used. Types of candidate substances are not specifically limited. Such candidate substances may be individual low molecular synthetic compounds or compounds that are present in extracts from natural substances. Alternatively, they may be compound libraries, phage display libraries, or combinatorial libraries. Preferably a candidate substance is a low molecular weight compound, and a compound library of low molecular weight compounds is preferable. Construction of such a compound library is known by persons skilled in the art. Furthermore, commercial compound libraries can also be used.

The transcriptional-activity-inhibiting substance of proteasome subunit α type 6 obtained by the aforementioned screening method is also encompassed in the scope of the present invention. Such a transcriptional-activity-inhibiting substance of proteasome subunit α type 6 is useful as a candidate substance for various drugs such as myocardial infarction therapeutic agents, anti-inflammatory agents, and immunosuppressants.

[6] Method for Screening for Transcriptional Regulatory Factor of Proteasome Subunit α Type 6

Furthermore, in the present invention, a transcriptional regulatory factor of proteasome subunit α type 6 can be screened by allowing a gene fragment containing a single nucleotide polymorphism of C/G at nucleotide −8 in the nucleotide sequence of exon 1 of the proteasome subunit α type 6 gene to come into contact with a sample wherein a transcriptional regulatory factor of proteasome subunit α type 6 is presumed to be present, and detecting the binding of the aforementioned fragment with the transcriptional regulatory factor. Such binding of a gene fragment containing the above single nucleotide polymorphism with a substance wherein a transcriptional regulatory factor of proteasome subunit α type 6 is presumed to be present can be detected by a gel-shift assay (electrophoretic mobility shift assay, EMSA), DNase I footprinting method, or the like. The gel-shift assay is preferable. In the gel shift method, when a protein (transcriptional regulatory factor) binds, the resulting molecular size becomes larger so as to lower the mobility of DNA in electrophoresis. Thus, a $^{32}$p-labeled gene fragment and a transcriptional regulatory factor are mixed, and then the resultant is subjected to gel electrophoresis. When the position of DNA is visualized by autoradiography, the shift of the factor-bound DNA is slow, so that it is detected as a band that shifts behind normal bands.

[7] Therapeutic Agent for Inflammatory Diseases

In the present invention, as described in the following examples, in the case of patients with myocardial infarction, it is highly likely that the nucleotide at position −8 in the nucleotide sequence of exon 1 of the proteasome subunit α type 6 gene is G. Thus, it was shown that the expression of proteasome subunit α type 6 is upregulated by this condition. This result demonstrated that proteasome subunit α type 6 is involved in the onset and progression of inflammatory diseases such as myocardial infarction. At the same time, it can be anticipated that inflammatory diseases such as myocardial infarction can be treated by suppressing the expression or activity of proteasome subunit α type 6. Moreover, as a means for suppressing the activity of proteasome subunit α type 6, a substance that inhibits the expression of proteasome subunit α type 6 due to RNAi or an antibody against proteasome subunit α type 6 can be used, for example.

Furthermore, therapeutic agents for inflammatory diseases, which comprise, as active ingredients, substances that suppress the expression or activity of proteasome subunit α type 6 are also encompassed within the scope of the present invention. Examples of such a substance that suppresses the expression or activity of proteasome subunit α type 6 used herein may include a low molecular weight compound, a substance that inhibits the expression of proteasome subunit α type 6 due to RNAi, and an antibody against proteasome subunit α type 6. A low molecular weight compound and a substance that inhibits the expression of proteasome subunit α type 6 due to RNAi are preferable.

RNAi (RNA interference) indicates a phenomenon whereby double-stranded RNA introduced into a cell suppresses the expression of a gene having the same sequence. Specific examples of a substance that inhibits the expression of proteasome subunit α type 6 due to RNAi include siRNA and shRNA as described below.

siRNA is an abbreviated name of short interfering RNA, and it is double-stranded RNA having a length of approximately 21 to 23 nucleotides. The form of siRNA is not particularly limited, as long as it causes RNAi. Examples of such siRNA include siRNA obtained by chemical synthesis, biochemical synthesis, or synthesis occurring in a living body, and short chain double-stranded RNA of 10 base pairs or more, which is obtained by decomposition of double-stranded RNA of approximately 40 bases or more in a living body. The sequence of siRNA is preferably 100% identical to the partial sequence of mRNA of proteasome subunit α type 6. However, the aforementioned sequences may not be necessarily 100% identical to each other.

It is preferable that a region having a homology between the nucleotide sequence of siRNA and the nucleotide sequence of the proteasome subunit α type 6 gene does not include a translation initiation region of the proteasome subunit α type 6 gene. Preferably, a sequence having a homology is apart from the translation initiation region of the proteasome subunit α type 6 gene at a distance of 20 nucleotides, and more preferably 70 nucleotides. An example of such a sequence having a homology may be a sequence around the 3'-terminus of the proteasome subunit α type 6 gene.

As a substance that inhibits the expression of proteasome subunit α type 6 due to RNAi, dsRNA of approximately 40 bases or more that causes siRNA and other substances may be used. For example, there can be used RNA having a double-stranded portion, which comprises a sequence exhibiting a homology of approximately 70% or more, preferably 75% or more, more preferably 80% or more, further preferably 85% or more, further more preferably 90% or more, particularly preferably 95% or more, and most preferably 100% with a portion of the nucleic acid sequence of the proteasome subunit α type 6 gene, or a modified body thereof. A sequence portion having a homology consists of at least 15 nucleotides, preferably approximately 19 nucleotides or more, more preferably 20 nucleotides or more, and further preferably 21 nucleotides or more.

As a substance that inhibits the expression of proteasome subunit α type 6 due to RNAi, shRNA (short hairpin RNA) having a short hairpin structure with a projection portion at the 3'-terminus thereof can also be used. shRNA indicates molecules consisting of approximately 20 base pairs or more, which form a hairpin-shaped structure as a result that single-stranded RNA partially contains a palindromic nucleotide sequence and thus that it has a double-stranded structure in a molecule thereof. Moreover, such shRNA preferably has a 3'-protruding terminus. The length of a double-stranded protion is not particularly limited. It is preferably 10 nucleotides or more, and more preferably 20 nucleotides or more. Herein, the 3'-protruding terminus is preferably DNA, more preferably DNA consisting of at least 2 nucleotides, and further preferably DNA consisting of 2 to 4 nucleotides.

Such a substance that inhibits the expression of proteasome subunit α type 6 due to RNAi may be artificially synthesized via chemical synthesis, or it may also be produced by synthesizing RNA from DNA having a hairpin structure formed by reversely ligating the DNA sequence of a sense strand to that of an antisense strand, in vitro, using T7 RNA polymerase. When the substance is synthesized in vitro, antisense and sense RNA portions can be synthesized from template DNA using T7 RNA polymerase and a T7 promoter. These RNA portions are annealed in vitro, and the annealed product is then introduced into a cell. As a result, RNAi takes place, and the expression of proteasome subunit α type 6 is thereby suppressed. Such introduction into a cell can be carried out by a calcium phosphate method or methods using various transfection reagents (e.g. oligofectamine, Lipofectamine, lipofection, etc.), for example.

As such a substance that inhibits the expression of proteasome subunit α type 6 due to RNAi, an expression vector comprising a nucleic acid sequence encoding the aforementioned siRNA or shRNA may also be used. Moreover, a cell comprising the aforementioned expression vector may further be used. The type of the aforementioned expression vector or cell is not particularly limited. Expression vectors or cells that have previously been used as medicaments are preferable.

Antibodies against proteasome subunit α type 6 can be prepared by standard methods. For example, polyclonal antibodies against proteasome subunit α type 6 can be obtained by immunizing mammals (e.g., mice, rats, rabbits, goats, sheep, or cattle) by a method known by persons skilled in the art using proteasome subunit α type 6 as an antigen, collecting blood from the mammals, and separating and purifying antibodies from the collected blood. When an antigen is administered, an appropriate adjuvant can also be used. Antibodies can be separated and purified from blood by general methods such as centrifugation, precipitation using ammonium sulfate or polyethylene glycol, and chromatography such as gel filtration chromatography, ion exchange chromatography, and affinity chromatography. On the other hand, monoclonal antibodies against proteasome subunit α type 6 can be prepared using hybridomas according to ordinary methods.

[8] Method for Screening for Therapeutic Agent for Inflammatory Diseases

In the present invention, it was shown that the enhanced expression or activity of proteasome subunit α type 6 is associated with inflammatory diseases. Thus, it was revealed that substances lowering the expression or activity of proteasome subunit α type 6 are useful as therapeutic agents for inflammatory diseases. According to the present invention, there is further provided a method for screening for a substance that lowers the expression or activity of proteasome subunit α type 6. An example of the above screening method can be carried out with the steps of allowing a cell to come into contact with a candidate substance; analyzing the expression level of a gene encoding proteasome subunit α type 6 within the cell; and selecting, as a therapeutic agent for an inflammatory disease, a candidate substance that lowers the expression level of the gene by comparison with a condition wherein the candidate substance is absent. Another example of the above screening method can be carried out with the steps of: allowing proteasome subunit α type 6 to come into contact with a candidate substance; measuring the activity of proteasome subunit α type 6; and selecting, as a therapeutic agent for an inflammatory disease, a candidate substance that lowers the proteasome subunit α type 6 activity by comparison with a condition wherein the candidate substance is absent. The term "proteasome subunit α type 6 activity" is used herein to mean, for example, activity of decomposing an IkB protein and activating NFkB.

As candidate substances, any substances can be used. Types of candidate substances are not specifically limited. For example, various libraries and the like described in [5] above in this specification can be used.

The present invention will be more specifically described in the following examples, but these examples are not intended to limit the scope of the present invention.

EXAMPLES

Example 1

Method

In the present example, 3,459 Japanese patients suffering from myocardial infarction searched by the Osaka Acute Coronary Insufficiency Study (OACIS) Group were used as subjects. The definite diagnosis of myocardial infarction was made according to the previous report (Ozaki K. et al., Nat Genet. 32, 650-654 (2002)). Control subjects were constituted with a general population of 3,955 people recruited through several Japanese medical institutions. All the subjects were Japanese people, and before participation in this study, written informed consent was obtained from them. Moreover, with regard to subjects of less than 20 years old, their parents' consent was obtained in accordance with procedures approved by Ethics Committee, the SNP Research Center (SRC), Riken, Yokohama. In the subsequent SNP analyses, the designing of PCR primers, a PCR experiment, DNA extraction, DNA sequencing, the discovery of SNP, identification of the genotype of SNP, and statistical analysis were carried out according to the previous reports (Ozaki K. et al., Nat Genet. 32, 650-654 (2002), and Ozaki, K. et al., Nature 429: 72-75 (2004)).

(Results)

First, the present inventors have hypothesized that a mutation in a gene encoding a proteasome protein would cause a risk of myocardial infarction. A 20S proteasome composed of a 7α-subunit and a 10β-subunit is a central granule of a 26S proteasome system (Coux, O., et al., Annu. Rev. Biochem. 65: 801-847 (1996)). Based on information from international HapMap database (hapmap.org) (The international HapMap consortium. The International HapMap Project. Nature 426: 789-796 (2003); and The international HapMap consortium. INTEGRATING ETHICS AND SCIENCE IN THE INTERNATIONAL HAPMAP PROJECT. Nature Reviews Genetics 5: 467-475 (2004)), and the JSNP database (snp.ims.u-tokyo.ac.jp) (Haga, H et al., J. Hum. Genet. 47: 605-610 (2002)), the present inventors have selected SNPs, which show a minor allele frequency of over 10% and which cover a majority of haplotypes in the genomic regions of genes encoding these subunits. Subsequently, the inventors have made a comparison among 450 patients suffering from myocardial infarction and 450 controls in terms of genotype frequency in such SNP loci (Tables 1 and 2). As a result, it has been revealed that a single SNP (dbSNP ID: rs1048990) (5'UTR −8C>G) of exon 1 of PSMA6 is significantly associated with myocardial infarction (Tables 1 and 2).

TABLE 1

Correlation analysis between myocardial infarction and SNPs in genes encoding 20S proteasome α- and β-subunits

| Gene name | dbSNP ID | MI | | | | Control | | | | Allele 1 vs allele 2 | | |
|---|---|---|---|---|---|---|---|---|---|---|---|---|
| | | 11 | 12 | 22 | Sum | 11 | 12 | 22 | Sum | $\chi^2$ | P | Odds ratio (95% CI) |
| PSMA1 | rs2597187 | 225 | 199 | 37 | 461 | 210 | 190 | 34 | 434 | 0.07 | 0.79 | 1.03 (0.84-1.26) |
| PSMA1 | rs11023246 | 120 | 256 | 94 | 470 | 99 | 243 | 96 | 438 | 1.07 | 0.30 | 1.10 (0.92-1.33) |
| PSMA1 | rs12286408 | 128 | 245 | 99 | 472 | 103 | 238 | 102 | 443 | 1.60 | 0.21 | 1.13 (0.94-1.35) |
| PSMA1 | rs2575843 | 424 | 44 | 0 | 468 | 399 | 44 | 0 | 443 | 0.07 | 0.79 | 1.06 (0.69-1.63) |
| PSMA1 | rs2575850 | 162 | 228 | 77 | 467 | 153 | 235 | 60 | 448 | 0.31 | 0.58 | 1.06 (0.88-1.27) |
| PSMA1 | rs7931378 | 219 | 195 | 50 | 464 | 201 | 199 | 46 | 446 | 0.15 | 0.70 | 1.04 (0.85-1.27) |
| PSMA1 | rs11023272 | 128 | 242 | 100 | 470 | 106 | 233 | 102 | 441 | 1.16 | 0.28 | 1.11 (0.92-1.33) |
| PSMA1 | rs10500802 | 229 | 214 | 37 | 480 | 237 | 188 | 29 | 454 | 1.93 | 0.16 | 1.15 (0.94-1.41) |
| PSMA1 | rs962025 | 223 | 189 | 50 | 462 | 194 | 196 | 45 | 435 | 0.52 | 0.47 | 1.08 (0.88-1.31) |
| PSMA2 | rs595541 | 348 | 93 | 13 | 454 | 336 | 104 | 4 | 444 | 0.10 | 0.75 | 1.05 (0.79-1.38) |
| PSMA2 | rs589882 | 377 | 79 | 1 | 457 | 355 | 77 | 3 | 435 | 0.25 | 0.62 | 1.09 (0.79-1.50) |
| PSMA2 | rs2288354 | 383 | 70 | 1 | 454 | 369 | 56 | 5 | 430 | 0.04 | 0.84 | 1.04 (0.73-1.47) |
| PSMA2 | rs643599 | 398 | 79 | 1 | 478 | 369 | 80 | 3 | 452 | 0.62 | 0.43 | 1.14 (0.83-1.56) |
| PSMA2 | rs678323 | 330 | 130 | 16 | 476 | 308 | 132 | 16 | 456 | 0.35 | 0.55 | 1.08 (0.85-1.37) |
| PSMA3 | rs6573194 | 204 | 205 | 56 | 465 | 172 | 219 | 49 | 440 | 0.75 | 0.39 | 1.09 (0.90-1.32) |
| PSMA3 | rs1885134 | 208 | 215 | 50 | 473 | 173 | 228 | 48 | 449 | 1.57 | 0.21 | 1.13 (0.93-1.37) |
| PSMA4 | rs3813570 | 127 | 202 | 114 | 443 | 103 | 158 | 93 | 354 | 0.00 | 0.98 | 1.00 (0.82-1.22) |
| PSMA5 | rs3820667 | 181 | 224 | 73 | 478 | 172 | 221 | 62 | 455 | 0.12 | 0.73 | 1.03 (0.86-1.25) |
| PSMA6 | rs8011465 | 304 | 151 | 13 | 468 | 263 | 160 | 12 | 435 | 1.41 | 0.23 | 1.15 (0.91-1.45) |
| PSMA6 | rs8008319 | 330 | 131 | 11 | 472 | 284 | 143 | 14 | 441 | 3.16 | 0.08 | 1.24 (0.98-1.58) |
| PSMA6 | rs7157492 | 326 | 130 | 11 | 467 | 283 | 145 | 15 | 443 | 3.73 | 0.05 | 1.27 (1.00-1.61) |
| PSMA6 | rs4982254 | 177 | 225 | 69 | 471 | 127 | 225 | 69 | 421 | 3.86 | 0.05 | 1.21 (1.00-1.46) |
| PSMA6 | rs1048990 | 185 | 222 | 66 | 473 | 216 | 194 | 41 | 451 | 9.56 | 0.002 | 1.36 (1.12-1.65) |
| PSMA6 | rs12878391 | 320 | 130 | 11 | 461 | 279 | 144 | 17 | 440 | 4.21 | 0.04 | 1.28 (1.01-1.63) |
| PSMA6 | rs4981283 | 255 | 192 | 22 | 469 | 222 | 187 | 31 | 440 | 2.28 | 0.13 | 1.17 (0.95-1.45) |
| PSMA6 | rs1957107 | 351 | 111 | 11 | 473 | 303 | 133 | 8 | 444 | 2.60 | 0.11 | 1.23 (0.96-1.59) |
| PSMA7 | rs2057169 | 328 | 133 | 13 | 474 | 292 | 147 | 13 | 452 | 2.41 | 0.12 | 1.21 (0.95-1.53) |
| PSMA7 | rs2057168 | 329 | 133 | 13 | 475 | 287 | 155 | 13 | 455 | 3.09 | 0.08 | 1.24 (0.98-1.56) |
| PSMA7 | rs2281739 | 333 | 134 | 13 | 480 | 297 | 147 | 13 | 457 | 1.64 | 0.20 | 1.17 (0.92-1.48) |
| PSMA7 | rs3746651 | 317 | 126 | 12 | 455 | 285 | 135 | 12 | 432 | 1.13 | 0.29 | 1.14 (0.89-1.46) |
| PSMA7 | rs2281740 | 325 | 132 | 12 | 469 | 282 | 151 | 12 | 445 | 2.83 | 0.09 | 1.23 (0.97-1.56) |
| PSMB1 | rs756519 | 276 | 179 | 25 | 480 | 258 | 169 | 26 | 453 | 0.07 | 0.79 | 1.03 (0.83-1.27) |
| PSMB1 | rs6914744 | 302 | 159 | 12 | 473 | 293 | 146 | 16 | 455 | 0.01 | 0.91 | 1.01 (0.81-1.28) |

TABLE 2

| PSMB2 | rs6668196 | 317 | 146 | 17 | 480 | 287 | 156 | 13 | 456 | 0.44 | 0.51 | 1.08 (0.86-1.36) |
|---|---|---|---|---|---|---|---|---|---|---|---|---|
| PSMB2 | rs6668101 | 252 | 190 | 35 | 477 | 219 | 208 | 27 | 454 | 0.59 | 0.44 | 1.08 (0.88-1.33) |
| PSMB3 | rs2019203 | 267 | 169 | 29 | 465 | 262 | 165 | 21 | 448 | 0.43 | 0.51 | 1.08 (0.87-1.33) |
| PSMB3 | rs228275 | 203 | 207 | 55 | 465 | 189 | 194 | 49 | 432 | 0.02 | 0.90 | 1.01 (0.83-1.23) |
| PSMB3 | rs65926 | 215 | 176 | 56 | 447 | 180 | 182 | 53 | 415 | 1.19 | 0.27 | 1.12 (0.92-1.37) |
| PSMB3 | rs228280 | 151 | 200 | 83 | 434 | 147 | 196 | 76 | 419 | 0.07 | 0.79 | 1.03 (0.87-1.24) |
| PSMB4 | rs2296840 | 132 | 218 | 120 | 470 | 114 | 223 | 109 | 446 | 0.09 | 0.76 | 1.03 (0.86-1.24) |
| PSMB4 | rs2479383 | 224 | 174 | 36 | 434 | 195 | 161 | 24 | 380 | 0.14 | 0.71 | 1.04 (0.84-1.30) |
| PSMB5 | rs3751498 | 322 | 137 | 14 | 473 | 301 | 124 | 19 | 444 | 0.20 | 0.65 | 1.06 (0.83-1.34) |
| PSMB5 | rs8021195 | 308 | 142 | 15 | 465 | 292 | 134 | 21 | 447 | 0.42 | 0.52 | 1.08 (0.86-1.37) |
| PSMB6 | rs2304975 | 159 | 228 | 58 | 445 | 160 | 198 | 66 | 424 | 0.01 | 0.91 | 1.01 (0.83-1.23) |
| PSMB6 | rs2304974 | 376 | 93 | 4 | 473 | 360 | 84 | 5 | 449 | 0.02 | 0.88 | 1.02 (0.76-1.38) |
| PSMB7 | rs3739477 | 410 | 39 | 2 | 451 | 387 | 61 | 2 | 450 | 4.82 | 0.03 | 1.56 (1.05-2.31) |
| PSMB7 | rs1041013 | 155 | 212 | 76 | 443 | 139 | 217 | 85 | 441 | 1.41 | 0.23 | 1.12 (0.93-1.35) |
| PSMB7 | rs7864941 | 298 | 144 | 31 | 473 | 303 | 129 | 14 | 446 | 5.05 | 0.03 | 1.30 (1.03-1.64) |
| PSMB7 | rs1330811 | 193 | 223 | 57 | 473 | 186 | 186 | 77 | 449 | 0.99 | 0.32 | 1.10 (0.91-1.33) |
| PSMB8 | rs3763364 | 210 | 210 | 53 | 473 | 215 | 181 | 49 | 445 | 0.88 | 0.35 | 1.10 (0.90-1.34) |
| PSMB8 | rs2071543 | 374 | 97 | 8 | 479 | 374 | 71 | 7 | 452 | 2.80 | 0.09 | 1.29 (0.96-1.74) |
| PSMB8 | rs2071541 | 351 | 115 | 8 | 474 | 319 | 110 | 15 | 444 | 1.38 | 0.24 | 1.17 (0.90-1.51) |
| PSMB8 | rs2071627 | 236 | 199 | 38 | 473 | 246 | 170 | 28 | 444 | 3.02 | 0.08 | 1.20 (0.98-1.48) |
| PSMB9 | rs4713600 | 183 | 228 | 68 | 479 | 174 | 228 | 53 | 455 | 0.33 | 0.56 | 1.06 (0.88-1.28) |
| PSMB9 | rs9276820 | 138 | 213 | 116 | 467 | 109 | 218 | 117 | 444 | 1.93 | 0.16 | 1.14 (0.95-1.37) |
| PSMB9 | rs3763348 | 177 | 221 | 74 | 472 | 175 | 222 | 49 | 446 | 2.02 | 0.16 | 1.15 (0.95-1.39) |
| PSMB9 | rs17587 | 256 | 183 | 30 | 469 | 258 | 161 | 28 | 447 | 0.65 | 0.42 | 1.09 (0.88-1.35) |
| PSMB10 | rs2301246 | 322 | 141 | 7 | 470 | 325 | 105 | 13 | 443 | 1.00 | 0.32 | 1.14 (0.88-1.4) |
| PSMB10 | rs2292318 | 355 | 113 | 6 | 474 | 338 | 100 | 8 | 446 | 0.01 | 0.91 | 1.02 (0.78-1.33) |

Furthermore, using such SNPs, a haplotype structure that completely covers the PSMA6 region was analyzed, and it was discovered that SNP associated with myocardial infarction is not in a linkage disequilibrium (LD) state with all other 7 SNPs existing within and around the PSMA6 region (Table 3).

TABLE 3

LD coefficients ($\gamma^2$) between pairs of SNPs in PSMA6 region

|  | rs8011465 | rs8008319 | rs7157492 | rs4982254 | rs1048990 | rs12878391 | rs4981283 | rs1957107 |
|---|---|---|---|---|---|---|---|---|
| rs8011465 | 1 | 0.74 | 0.72 | 0.17 | 0.13 | 0.71 | 0.59 | 0.49 |
| rs8008319 |  | 1 | 0.96 | 0.15 | 0.11 | 0.95 | 0.48 | 0.57 |
| rs7157492 |  |  | 1 | 0.15 | 0.11 | 0.99 | 0.51 | 0.61 |
| rs4982254 |  |  |  | 1 | 0.36 | 0.15 | 0.23 | 0.11 |
| rs1048990 |  |  |  |  | 1 | 0.12 | 0.09 | 0.58 |
| re1287839 |  |  |  |  |  | 1 | 0.5 | 0.61 |
| rs4981283 |  |  |  |  |  |  | 1 | 0.5 |
| rs1957107 |  |  |  |  |  |  |  | 1 |

There were no particular haplotypes existing in the PSMA6 region that exhibited statistical significance in correlation with myocardial infarction (P>0.01). Subsequently, in order to examine the possibility of other unidentified SNPs of this gene to cause a risk of myocardial infarction, genomic DNAs derived from 48 Japanese people were subjected to sequencing again, and SNP was searched through 29-kb regions including PSMA, from which a region corresponding to a repeated sequence had been eliminated. As a result, total 13 SNPs were identified (FIG. 1a). When compared with the dbSNP database of the National Center for Biotechnology Information, 7 out of 13 SNPs (5'-flanking; −18T/C and −1C/T, intron 1; 1233A/T, 1246A/G, 7239A/G, 7294T/A, and 7693G/A) were novel. These 13 SNP genotypes were identified with regard to approximately 100 myocardial infarction patients and 100 controls. As a result, it was revealed that the minor allele frequency of only 3 SNPs (exon 1 −8C/G (rs1048890), intron 1 1233A/T and intron 1 10820A/G (rs12878391)) exceeded 5% (FIG. 1a). In the first screening, the correlation of intron 1 10820 A/G with myocardial infarction was not observed (Table 1), and the remaining two SNPs were perfectly LD (linkage disequilibrium) ($\gamma^2$=1). Thus, the genotypes of 2,592 patients with myocardial infarction and 2,851 controls were identified, so as to examine the SNP of exon 1 −8C/G. As a result, it was discovered that there is a strong correlation between such SNP and myocardial infarction ($\chi^2$=21.10, p=0.0000044, comparison of allele frequency, FIG. 1b). In order to confirm this correlation, independent panels consisting of other myocardial infarction patients and controls who have recently been gathered (867 myocardial infarction patients and 1,104 controls) were used to further examine such correlation. As a result, the correlation with myocardial infarction was the same as the previous result ($\chi^2$=9.02, p=0.0027, recessive-associated models, Table 4).

TABLE 4

| Genotype PSMA6 | | | χ2 [P value] (Odds ratio) <95% CI> | |
|---|---|---|---|---|
| exon1 -8 C > G* | MI (%) | Control (%) | Allele frequency | GG vs others |
| CC | 355 (40.9) | 479 (43.4) | 5.19 | 9.02 |
| CG | 380 (43.8) | 507 (45.9) | [0.023] | [0.0027] |
| GG | 132 (15.2) | 118 (10.7) | (1.17) | (1.50) |
| Total | 867 | 1,104 | <1.02-1.33> | <1.15-1.96> |

*Nucleotide number is based on naming of mutation.

Example 2

Luciferase Assay (Method)

DNA fragments that corresponded to nt-600 in the 5'-flanking region to 10 of exon 1 of PSMA6 and nt 1133 to nt 1343 of intron 1 were cloned into a pGL3-basic vector (manufactured by Promega) upstream of a luciferase gene in the 5'-3' direction. After transfection for 48 hours, cells were dissolved in a passive lysis buffer (manufactured by Promega), and the luciferase activity thereof was then measured using a Dual-Luciferase Reporter Assay System (manufactured by Promega).

(Results)

In order to confirm whether or not two SNPs of PSMA5, namely, −8C/G of exon 1 and/or 1233A/T of intron 1 have an influence on the expression level thereof, 4 types of plasmid clones including DNA fragments corresponding to such SNPs were constructed. Each construct had genomic fragments containing SNPs of exon 1, genomic fragments containing SNPs of intron 1 (each haplotype such as −8C-1233A, −8G-1233A, −8C-1233T, and −8G-1233T), and a luciferase gene transcription unit, in the 5'-3' direction. As shown in FIG. 2, two clones containing the −8G-1233A haplotype and the −8G-1233T haplotype exhibited transcriptional activity that was 1.5 to 1.7 times higher than that of two other clones containing two other haplotypes. This demonstrates that not displacement in intron 1 but displacement in exon 1 has an influence on the transcription level of PSMA6.

Example 3

Gel Shift Assay (Method)

According to the previous report (Andrews, N. C. et al., Nucleic Acid Res. 11, 2499 (1991)), a nuclear extract prepared from HepG2 cells was incubated together with 3 tandem copies of 16 oligonucleotides (from −15 to 1 of exon 1 of PSMA6) labeled with digoxigenin (DIG) −11-dUTP, in the presence of MgCl$_2$ and CaCl$_2$, using a DIG gel shift kit (manufactured by Roche). The reaction was carried out without Poly[I(dc)] reagents at room temperature. As a competitive test, a nuclear extract had previously been incubated together with unlabeled oligonucleotides (125 times more excessive) before addition of the DIG-labeled oligonucleotides. A protein/DNA complex was separated on a native polyacrylamide gel (6%) (manufactured by Invitrogen) in a 0.5×Tis/Borate/EDTA (TBE) buffer, and it was then transferred onto a nitrocellulose membrane. A signal was detected using a chemiluminescent detection system (manufactured by Roche) in accordance with instruction for use.

(Results)

It was presumed that there were no known proteins that bind to the DNA fragments of Example 2 above. Herein, the presence or absence of a nuclear factor that may bind to an oligonucleotide corresponding to the genome sequence of a −8C allele or a −8G allele was examined. When a nuclear extract derived from HepG2 cells was used, a single band showing that a nuclear protein binding to the oligonucleotide was observed not in a lane corresponding to the C allele but in a lane corresponding to the G allele (FIG. 2c). This result suggested the possibility that an unidentified nuclear factor interacting with this region may control the transcription of PSMA6, and further that it may influence on myocardial infarction sensitivity.

Example 4

Quantification of Change in Allele Expression (Method)

A B cell line transformed with EBV was obtained from the Riken Bioresource Center. From 7 cell lines having a heterozygous genotype at the SNP site of −8C/G of exon 1, mRNA was prepared. Thereafter, cDNA was synthesized from the mRNA. According to the previous report (Shuen Lo, H et al. Genome Res. 13: 1855-1862 (2003)), an allele expression experiment was carried out by a TaqMan assay using the following primers and allele-specific probes.

```
Forward primer:
5'-GGGCCCAGGGATTGTGTT          (SEQ ID NO: 3)

Reverse primer:
5'-AATGGTAATGTGGCGGTCAAA       (SEQ ID NO: 4)

C allele-specific probe:
5'-FAM-AAGTAGTGCTTCTACCAAC     (SEQ ID NO: 5)

G allele-specific probe:
5'-VIC-AAGTAGTGCTTGTACCAAC     (SEQ ID NO: 6)
```

(All primers and probes used in the TaqMan assay were synthesized by Applied Biosystems.) The PCR reaction was carried out using ABI PRISM 7700 Sequence Detection System (manufactured by Applied Biosystems) under the following conditions: 90° C.-10 minutes performed once, and 40 cycles of 92° C.-0.25 minutes and 60° C.-1 minute.

(Results)

In order to confirm the effect of the SNP of the present invention on transcription, using TaqMan probes, allele-specific quantitative PCR was performed on 7 individual EBV-transformed human B cell lines (HEY cell lines). Such HEY cell lines were collected from individual people having heterozygous genotype at the −8C/G SNP gene locus. With regard to the expression level of PSMA6 in these cell lines, the G allele was 1.7 to 1.8 times higher than the C allele (Table 5). This experimental result and the results of Examples 2 and 3 demonstrate that the SNP in exon 1 of the PSMA6 of the present invention has an influence on the transcription level in vitro and in vivo.

TABLE 5

Allele change in expression level of PSMA6

| | HEV32 | HEV36 | HEV38 | HEV40 | HEV43 | HEV51 | HEV52 |
|---|---|---|---|---|---|---|---|
| G/C ratio | 1.68 ± 0.02 | 1.72 ± 0.02 | 1.77 ± 0.01 | 179 ± 0.04 | 1.70 ± 0.02 | 1.69 ± 0.04 | 1.71 ± 0.06 |

G/C ratio is indicated as a mean value ± SD for each cell line.

Each sample was subjected to 3 times of tests in a single assay, and each assay was independently repeated 3 times.

Example 5 siRNA Experiment and Western Blot Analysis (Method)
(siRNA Experiment)

The target sequence (5'-GTGTGATCCTGCAGGTTAC-3') (SEQ ID NO: 7) of PSMA6 was cloned into a pSilencer 2.0-U6 siRNA vector (manufactured by Ambion). A pSilencer negative control vector (manufactured by Ambion) was used as a negative control. A pNifty plasmid vector, a luciferase reporter vector to which a NFkB-specific E-selectin promoter has been ligated (manufactured by Invitrogen), and a pRL-TK vector used as an internal standard (manufactured by Promega) were co-transfected by a Nucleofector system (manufactured by Amaxa). Thereafter, Jurkat cells were stimulated with PMA (20 ng/ml) for 2 hours, and the cells were then recovered. The luciferase activity was then measured using a Dual-Luciferase Reporter Assay System (manufactured by Promega). For an experiment using human coronary artery endothelial cells (HCAEC) (Sanko Junyaku Co., Ltd.), a pSilencer 5.1-U6 retro system (manufactured by Ambion) was used to establish a stable pT67 cell line that constitutionally expresses retrovirus PSMA6 siRNA. HCAEC was infected with the supernatant of such a stable pT67 cell line for 72 hours, and they were then transfected with the pNiFty vector. After completion of the transfection for 24 hours, the Dual-Luciferase Reporter Assay System was used to measure luciferase activity, and it was then standardized by comparing with a whole cell protein concentration. mRNA was quantified according to the previous report (Ozaki K. et al., Nat Genet 32, 650-654 (2002)).

(Western Blot Analysis)

As with the aforementioned siRNA experiment, HCAEC cells were transfected with PSMA6 and control siRNA. The cells were stimulated with 20 ng/ml PMA (manufactured by Sigma) for 0, 5, 10, 15, and 45 minutes. Thereafter, the cells were recovered and dissolved in a standard SDS-sample buffer. After performing SDS-PAGE and blotting, IkB-α, a rabbit polyclonal antibody (manufactured by Cell Signaling) against phosphorylated IkB-α, and a horseradish peroxidase-labeled rabbit secondary antibody (manufactured by Amersham) or human α tubulin (manufactured by Santa Cruz) and a horseradish peroxidase-labeled anti-mouse IgG antibody (manufactured by Amersham) were used to visualize immune complexes.

(Results)

Decomposition of an IkB protein is a step essential for activation of NFkB acting as a main transcriptional factor that regulates the expression of an inflammatory gene. A proteasome complex plays an important role in this decomposition process. Thus, whether or not the decomposition of IkB and the subsequent activation of NFkB are influenced by the intracellular level of a PSMA6 protein was examined using a siRNA (small interference RNA) technique. As shown in FIG. 3, single siRNA to PSMA6 significantly suppressed the mRNA level of the PSMA6 (FIG. 3a: Jurkat cells; and FIG. 3b: human coronary artery endothelial cells (HCAEC)), and thereby, the NFkB activity was inhibited both in the Jurkat cells and in the HCAEC (FIGS. 3c and 3d). Further, the effect of siRNA was examined in a state of being stimulated with PMA. As a result, IkB was phosphorylated by PMA stimulation within 5 minutes, and it was decomposed within 15 minutes in HCAEC treated with control siRNA (FIG. 3e, right panel). However, when the cells were treated with PSMA6-specific siRNA, decomposition of phosphorylated IkB was significantly retarded (FIG. 3e, left panel). These results suggested the possibility that the physiological function of ubiquitin-proteasome may be damaged by a change in PSMA6 expression and that it may have an influence on the expression of a gene associated with a NFkB dependent inflammatory pathway.

Example 6

Increase in Risk Rate of Myocardial Infarction Due to Combination of SNPs of LTA, Galectin-2 and PSMA6 (Based on Results from 3,000 People for Each)

The following conditions were applied:
All the SNPs have genotypes that are not involved in myocardial infarction: genotype 0
One of the SNPs has a genotype causing risk: genotype 1
Two of the SNPs have genotypes causing risk: genotype 2
All the three SNPs have genotypes causing risk: genotype 3

The risk rate (odds ratio) of myocardial infarction in genotypes 0 to 3 is shown in the following Table 6.

TABLE 6

| Genotype | Odds ratio |
|---|---|
| 0 | 1 |
| 1 | 1.9 |
| 2 | 2.43 |
| 3 | 3.73 |

INDUSTRIAL APPLICABILITY

According to the method of the present invention, the judgment of the presence or absence of the onset of inflammatory diseases including myocardial infarction as a typical example and the judgment of the probability of the onset of such a disease can be performed accurately and rapidly.

BRIEF DESCRIPTION OF THE DRAWINGS

FIG. 1 shows the correlation of SNPs in PSMA6 with myocardial infarction. FIG. 1a shows the map of SNPs in PSMA6 gene locus. The minor allele frequency of each SNP of approximately 200 Japanese people is indicated within parentheses. FIG. 1B shows the correlation of myocardial infarction with SNPs of exon 1 of PSMA6. Nucleotide numbers were used in accordance with mutation nomenclature (Den Dunnen, J. T. et al. Hum. Mutat. 15: 7-12 (2000)).

FIG. 2 shows the transcriptional control activity of SNP of exon 1 of PSMA6 in HeLa cells (a) and HepG2 cells (b). Each experiment was repeated 3 times, and 3 samples were prepared and used in each study. The symbol * indicates a student T test, and FIG. 2c shows the binding of an unknown nuclear factor to exon 1 of PSMA6. The arrow indicates a band showing the specific bond of a nuclear factor to a G allele.

FIG. 3 shows that the expression level of PSMA6 has an influence on activation of NFkB and decomposition of IkB. FIGS. 3a and 3b show PSMA6 mRNA NA level in random siRNA-treated or PSMA6 siRNA-treated Jurkat cells (a) and HCAEC cells (b). FIGS. 3c and 3d show relative NFkB activity in Jurkat cells (c) and in HCAEC cells (d). Each experiment was repeated 3 times, and 3 samples were prepared and used in each study. FIG. 3e shows inhibition of phosphorylated IkB-α decomposition in HCAEC by knock-down of PSMA6.

The invention claimed is:

1. A method for determining that a human subject has or is at risk of developing myocardial infarction, said method comprising:
   detecting, in a nucleic acid present in a sample of biological material removed from the subject, a G/G homozygous state at position −8 of the human PSMA6 gene, wherein position −8 is position −8 of the 5' UTR and is numbered relative to the start site;
   wherein detecting the G/G homozygous state indicates the presence of, or a risk of developing, myocardial infarction in the subject.

* * * * *